US010406349B2

(12) United States Patent
Shi et al.

(10) Patent No.: US 10,406,349 B2
(45) Date of Patent: Sep. 10, 2019

(54) MEDICAL LEADS AND TECHNIQUES FOR MANUFACTURING THE SAME

(71) Applicant: Medtronic, Inc., Minneapolis, MN (US)

(72) Inventors: Alan Shi, Plymouth, MN (US); Darren A. Janzig, Center City, MN (US); Bernard Q. Li, Plymouth, MN (US); Richard T. Stone, Minneapolis, MN (US); Dale F. Seeley, Spring Park, MN (US); Peng Cong, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 883 days.

(21) Appl. No.: 14/206,650

(22) Filed: Mar. 12, 2014

(65) Prior Publication Data
US 2014/0343644 A1 Nov. 20, 2014

Related U.S. Application Data

(60) Provisional application No. 61/792,406, filed on Mar. 15, 2013.

(51) Int. Cl.
*A61N 1/05* (2006.01)
*A61N 1/375* (2006.01)

(52) U.S. Cl.
CPC .............. *A61N 1/05* (2013.01); *A61N 1/375* (2013.01)

(58) Field of Classification Search
CPC .................................. A61N 1/05; A61N 1/375
USPC ........................................ 607/116; 427/2.24
See application file for complete search history.

(56) References Cited

U.S. PATENT DOCUMENTS

| 4,602,637 | A | 7/1986 | Elmqvist et al. |
| 5,203,348 | A * | 4/1993 | Dahl et al. ............... 607/129 |
| 5,603,732 | A | 2/1997 | Dahl et al. |
| 5,609,611 | A | 3/1997 | Bolz et al. |
| 5,632,770 | A | 5/1997 | Schaldach |
| 6,263,250 | B1 | 7/2001 | Skinner |
| 7,079,903 | B2 | 7/2006 | O'Brien |
| 7,603,169 | B2 | 10/2009 | Kruger et al. |

(Continued)

FOREIGN PATENT DOCUMENTS

EP 1454651 A1 9/2004

OTHER PUBLICATIONS

International Search Report and Written Opinion from international application No. PCT/US2014/026386, dated May 22, 2014, 11 pp.

(Continued)

*Primary Examiner* — Alyssa M Alter
(74) *Attorney, Agent, or Firm* — Shumaker & Sieffert, P.A.

(57) ABSTRACT

In some examples, the disclosure relates to a medical device comprising a lead including an electrically conductive lead wire; and an electrode electrically coupled to the lead wire, the electrode including a substrate and a coating on an outer surface of the substrate, wherein the lead wire is formed of a composition comprising titanium or titanium alloys, wherein the substrate is formed of a composition comprising one or more of titanium, tantalum, niobium, and alloys thereof, wherein the coating comprises at least one of Pt, TiN, IrOx, and poly(dioctyl-bithiophene) (PDOT). In some examples, the lead wire may be coupled to the lead wire via a weld, such as, e.g., a laser weld.

30 Claims, 46 Drawing Sheets

(56) References Cited

U.S. PATENT DOCUMENTS

| | | |
|---|---|---|
| 7,666,523 B2 | 2/2010 | Zhou |
| 7,856,707 B2 | 12/2010 | Cole |
| 8,000,808 B2 | 8/2011 | Hegland et al. |
| 2005/0007718 A1 | 1/2005 | Stevenson et al. |
| 2005/0084672 A1 | 4/2005 | O'Brien |
| 2006/0167536 A1 | 7/2006 | Nygren et al. |
| 2007/0239249 A1 | 10/2007 | Tockman et al. |
| 2008/0161886 A1 | 7/2008 | Stevenson et al. |
| 2010/0075168 A1 | 3/2010 | Schaffer |
| 2011/0072659 A1 | 3/2011 | Swanson et al. |
| 2011/0130803 A1 | 6/2011 | McDonald |
| 2011/0270330 A1 | 11/2011 | Janzig et al. |
| 2012/0123318 A1 | 5/2012 | Ek et al. |
| 2012/0296405 A1 | 11/2012 | Thenuwara et al. |

OTHER PUBLICATIONS

U.S. Appl. No. 14/209,799, Xingfu Chen, filed Mar. 13, 2014.
International Preliminary Report on Patentability from International Application No. PCT/US2014/026386, dated Sep. 24, 2015, 8 pp.
Response to Office Action dated Nov. 27, 2015, from U.S. Appl. No. 14/209,799, filed Feb. 29, 2016, 17 pp.
Final Office Action from U.S. Appl. No. 14/209,799, dated Apr. 21, 2016, 17 pp.
Examiner's Answer to Appeal Brief filed on Oct. 24, 2016, from U.S. Appl. No. 14/209,799, dated Dec. 15, 2016, 8 pp.
Advisory Action from U.S. Appl. No. 14/209,799, dated Aug. 3, 2016, 8 pp.
Notice of Appeal from U.S. Appl. No. 14/209,799, filed Aug. 22, 2016, 2 pp.
Pre-Appeal Brief Request for Review for U.S. Appl. No. 14/209,799, filed Aug. 22, 2016, 6 pp.
Office Action from U.S. Appl. No. 14/209,799, dated Nov. 27, 2015, 19 pp.
Response to Office Action dated Apr. 21, 2016, from U.S. Appl. No. 14/209,799, filed Jul. 21, 2016, 12 pp.
Reply Brief to Examiner's Answer dated Dec. 15, 2016, from U.S. Appl. No. 14/209,799, filed Feb. 15, 2017, 10 pp.
Notice of Allowance from U.S. Appl. No. 14/209,799, dated Sep. 24, 2018, 7 pp.
Decision on Appeal from U.S. Appl. No. 14/209,799, dated May 16, 2018, 8 pp.
Notice of Allowance from U.S. Appl. No. 14/209,799, dated Jun. 8, 2018, 8 pp.

\* cited by examiner

MEDICAL LEADS AND TECHNIQUES FOR MANUFACTURING THE SAME

This application claims the benefit of U.S. Provisional Application No. 61/792,406, filed on Mar. 15, 2013, the entire content of which is incorporated herein by reference.

TECHNICAL FIELD

The present disclosure relates to medical devices, more particularly to medical device leads and electrodes configured for delivery of electrical stimulation therapy and/or sensing of electrical signals.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

SUMMARY

Some examples of the present disclosure relate to medical device leads including one or more electrodes for use in medical device systems. The one or more electrodes may include a surface coating deposited on a titanium or titanium alloy electrode substrate. The electrode substrate may be welded or otherwise coupled to a lead wire of the lead that is also formed of a titanium or titanium alloy. The surface coating may be formed of a Pt, TiN, IrOx, and poly(dioctyl-bithiophene) (PDOT) composition.

In one example, the disclosure relates to a medical device comprising a lead including an electrically conductive lead wire; and an electrode electrically coupled to the lead wire, the electrode including a substrate and a coating on an outer surface of the substrate, wherein the lead wire is formed of a composition comprising titanium or titanium alloys, wherein the substrate is formed of a composition comprising one or more of titanium, tantalum, niobium, and alloys thereof, wherein the coating comprises at least one of Pt, TiN, IrOx, and poly(dioctyl-bithiophene) (PDOT).

In another example, the disclosure relates to a method for forming a medical device lead, the method comprising electrically coupling a lead including an electrically conductive lead wire to an electrode, the electrode comprising a substrate having an outer surface; and depositing a coating on the outer surface of the substrate, wherein the lead wire is formed of a composition comprising titanium or titanium alloys, wherein the substrate is formed of a composition comprising one or more of titanium, tantalum, niobium, and alloys thereof, wherein the coating comprises at least one of Pt, TiN, IrOx, and poly(dioctyl-bithiophene) (PDOT).

The details of one or more aspects of the disclosure are set forth in the accompanying drawings and the description below. Other features, objects, and advantages will be apparent from the description and drawings, and from the claims.

DETAILED DESCRIPTION

Figure 1:
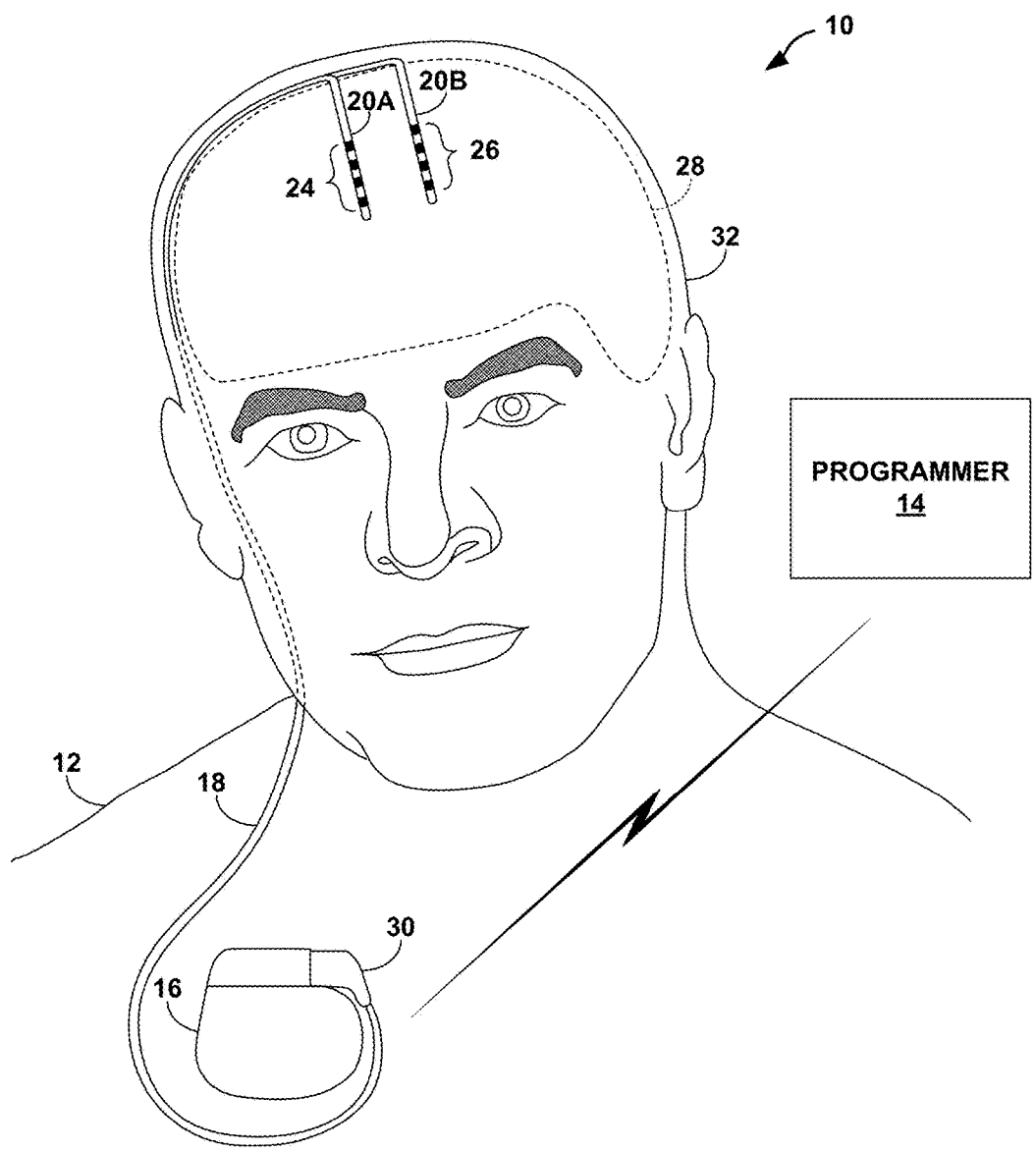
FIG. 1 is a conceptual diagram illustrating an example medical device system.

As described above, some examples of the disclosure relate to medical device leads (also referred to as "medical leads" or "leads") including one or more electrodes. Using the lead and electrode, a medical device may deliver and/or sense electrical signals to provide therapy to a patient to treat a patient condition. Medical leads may include a conductive electrode member electrically and mechanically connected to one or more conductive lead wires extending through the lead body. Electrical stimulation from a medical device may be conductive along the lead to be delivered across the electrode surface.

In some examples, the electrode and lead wires of a medical lead may each be formed of materials having substantially the same or similar composition. For example, one lead design includes one or more platinum iridium electrodes mounted on the distal end of a lead including a platinum or platinum iridium (Pt—Ir) lead wire. Each of the electrodes may be electrically and mechanically coupled to the Pt—Ir lead wire via lasing welding. In some examples, bare Pt-10Ir may be used as an electrode material for medical device leads. However, in some instances, a Pt-10Ir electrode may not support high charge injection density without inducing corrosion on the electrode itself, e.g., in certain applications where the charge density limit requirement is relatively very high. Further, in addition to being relatively expensive in comparison to other metals, in order to suit more magnetic resonance imaging (MRI) compatible medical device systems, materials other than that of Pt—Ir lead wires and electrodes may be desirable.

In some instances, conductor materials such as titanium alloys (e.g., Ti-15Mo) or other low modulus beta titanium alloys, which have high electrical resistance to help reduce MRI induced heating of tissue adjacent to electrodes, may be used to form a lead wire. Further, Ti and Ti alloys, and Ti-15Mo alloys in particular, may exhibit superior fatigue life, e.g., as compared to that of Pt or Pt—Ir lead wires. However, such materials may not be desirable to form the portion of the lead electrode in direct contact with body tissue. For example, in some instances, Ti and alloys may have a relatively low charge density compared to that of Pt based alloys, which may decrease the effectiveness for delivering electrical stimulation.

While providing for MRI compatibility in a medical lead, laser welding dissimilar metals such as Pt—Ir and titanium alloys can be difficult. For example, micro cracking may occur in an intermetallic layer when a titanium alloy and Pt—Ir are welded together, which may impose a reliability concern.

In accordance with examples of the disclosure, medical lead designs including an electrode formed of substrate comprising one or more of titanium, tantalum, niobium, and alloys thereof that is bonded to a titanium or titanium alloy lead wire. A thin coating may be applied to the outer surface of the electrode substrate. The surface coating may comprise at least one of Pt, TiN, IrOx, and poly(dioctyl-bithiophene) (PDOT). A Pt, TiN, IrOx coating may be applied via any suitable technique including, e.g., sputtering such as vacuum sputtering. Electropolymerization of PDOT may be used to form a conductive coating on the outer surface of the titanium or titanium alloy electrode substrate.

Example coated electrode designs in medical leads may allow may allow for one or more advantages. For example, a surface coated electrode substrate comprising one or more of titanium, tantalum, niobium, and alloys thereof may provide an electrode capable of supporting relatively high charge density limits e.g., due to increased effective surface area and surface roughness compared to that of the surface of the uncoated electrode substrate Moreover, such an electrode may exhibit reduced electrode tissue impedance compared to a bare 90Pt-10Ir electrode. Such an electrode may allow for design freedom such as further miniaturization of parts and reduced pitch of leads. In addition to reduced cost of materials compared to that of the Pt or Pt—Ir electrodes, the electrode substrate may be reliably bonded, e.g., via laser welding, to a titanium or titanium alloy lead wire due the similar compositions. As noted above, a titanium or titanium alloy lead wire may reduce tissue heating adjacent to electrodes during MRI scanning of a medical device system employing such a lead.

FIG. 1 is a conceptual diagram illustrating an example stimulation system with a stimulation lead implanted in the brain of a patient. As shown in FIG. 1, stimulation system 10 includes implantable medical device (IMD) 20, lead plug 22, lead wire 24, lead 14 and one or more electrodes 15 implanted within patient 12. Specifically, lead 14 enters through cranium 16 and is implanted within brain 18 to deliver DBS. One or more electrodes 15 of lead 14 provides electrical pulses to surrounding anatomical regions of brain 18 in a therapy that may alleviate a condition of patient 12. In some examples, more than one lead 14 may be implanted within brain 18 of patient 12 to stimulate multiple anatomical regions of the brain. As shown in FIG. 1, system 10 may also include a programmer 19, which may be a handheld device, portable computer, or workstation that provides a user interface to a clinician. The clinician interacts with e user interface to program stimulation parameters.

For ease of illustration, examples of the disclosure will primarily be described with regard to implantable electrical stimulation leads and implantable medical devices that neurostimulation therapy to a patient's brain in the form of DBS. However, the features and techniques described herein may be useful in other types of medical device systems, which may include other types of implantable medical leads for use with medical devices, such as, e.g., implantable medical devices (IMDs). For example, the features and techniques described herein may be used in systems with medical devices that deliver stimulation therapy to a patient's heart, e.g., pacemakers, and pacemaker-cardioverter-defibrillators. As other examples, the features and techniques described herein may be embodied in systems that deliver other types of neurostimulation therapy (e.g., spinal cord stimulation or sacral nerve stimulation), stimulation of at least one muscle or muscle groups, stimulation of at least one organ such as gastric system stimulation, stimulation concomitant to gene therapy, and, in general, stimulation of any tissue of a patient.

Therapy system 10 includes medical device programmer 14, implantable medical device (IMD) 16, lead extension 18, and one or more leads 20A and 20B (collectively "leads 20) with respective sets of electrodes 24, 26. IMD 16 includes a stimulation therapy module that includes an electrical stimulation generator that generates and delivers electrical stimulation therapy to one or more regions of brain 28 of patient 12 via a subset of electrodes 24, 26 of leads 20A and 20B, respectively. In the example shown in FIG. 1, therapy system 10 may be referred to as a DBS system because IMD 16 provides electrical stimulation therapy directly to tissue within brain 28, e,g., a tissue site under the dura mater of brain 28. In other examples, leads 20 may be positioned to deliver therapy to a surface of brain 28 (e.g., the cortical surface of brain 28).

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to PAD 16 via connector block 30 (also referred to as a header), which may include, for example, electrical contacts that electrically couple to respective electrical contacts on lead extension 18. The electrical contacts electrically couple the electrodes 24, 26 carried by leads 20 to 16. Lead extension 18 traverses from the implant site of IMD 16 within a chest cavity of patient 12, along the neck of patient 12 and through the cranium of patient 12 to access brain 28. Generally, IMD 16 is constructed of a biocompatible material that resists corrosion and degradation from bodily fluids. IMD 16 may comprise a hermetic housing 34 to substantially enclose components, such as a processor, therapy module, and memory.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Although FIG. 1 illustrates system 10 as including two leads 20A and 20B coupled to IMD 16 via lead extension 18, in some examples, system 10 may include one lead or more than two leads.

Leads 20 may deliver electrical stimulation via electrodes 24, 26 to treat any number of neurological disorders or diseases in addition to movement disorders, such as seizure disorders or psychiatric disorders. Leads 20 may be implanted within a desired location of brain 28 via any suitable technique, such as through respective burr holes in a skull of patient 12 or through a common burr hole in the cranium 32. Leads 20 may be placed at any location within brain 28 such that electrodes 24, 26 of leads 20 are capable of providing electrical stimulation to targeted tissue during treatment. In the examples shown in FIG. 1, electrodes 24, 26 of leads 20 are shown as ring electrodes. In other examples, electrodes 24, 26 of leads 20 may have different configurations including segmented electrodes or paddle electrodes. Electrodes 24, 26 of leads 20 may have a complex electrode array geometry that is capable of producing shaped electrical fields. In this manner, electrical stimulation may be directed to a specific direction from leads 20 to enhance therapy efficacy and reduce possible adverse side effects from stimulating a large volume of tissue.

In accordance with one or more examples of the disclosure, electrodes 24 and 26 may include an electrode substrate formed of a titanium or titanium alloy material. As noted above, in some examples, the electrode substrate for each of electrodes 24, 26 may include a coating deposited on the outer surface of the electrode substrate. The surface coating may comprise at least one of Pt, TiN, IrOx, and poly(dioctyl-bithiophene) (PDOT). The electrode substrates may be mechanically and electrically coupled to a lead wire (not shown) formed of a titanium or titanium alloy material within leads 20.

IMD 16 may deliver electrical stimulation therapy to brain 28 of patient 12 according to one or more stimulation therapy programs. A therapy program may define one or more electrical stimulation parameter values for therapy generated and delivered from IMD 16 to brain 28 of patient 12. Where IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 12, therapy system 10 monitors one or more bioelectrical brain signals of patient 12. For example, IMD 16 may include a sensing module that senses bioelectrical brain signals within one or more regions of brain 28. In the example shown in FIG. 1, the signals generated by electrodes 24, 26 are conducted to the sensing module within IMD 16 via conductors within the respective lead 20A, 20B. As described in further detail below, in some examples, a processor of IMD 16 may sense the bioelectrical signals within brain 28 of patient 12 and controls delivery of electrical stimulation therapy to brain 28 via electrodes 24, 26.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). In other examples, programmer 14 may be a larger workstation or a separate application within another multifunction device, rather than a dedicated computing device. For example, the multi-function device may be a notebook computer, tablet computer, workstation, cellular phone, personal digital assistant or another computing device that may run an application that enables the computing device to operate as a secure medical device programmer 14.

Figure 2:
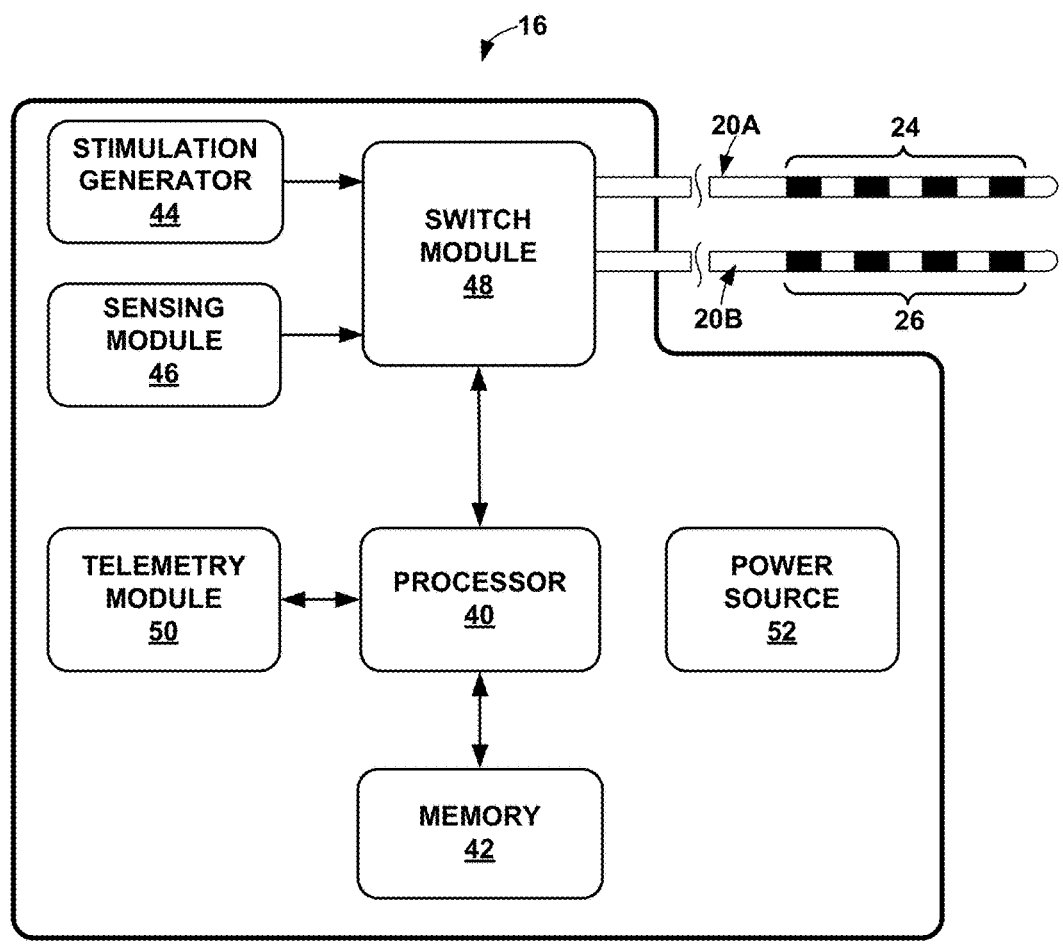
FIG. 2 is a conceptual diagram illustrating an example implantable medical device.

FIG. 2 is a functional block diagram illustrating components of IMD 16. In the example shown in FIG. 2, IMD 16 includes memory 40, processor 42, stimulation generator 44, sensing module 46, switch module 48, telemetry module 50, and power source 52. Processor 42 may include any one or more microprocessors, controllers, digital signal processors (DSPs), application specific integrated circuits (ASICs), field-programmable gate arrays (FPGAs), and discrete logic circuitry. The functions attributed to processors described herein, including processor 42, may be provided by a hardware device and embodied as software, firmware, hardware, or any combination thereof.

In the example shown in FIG. 2, sensing module 46 senses bioelectrical brain signals of patient 12 via select combinations of electrodes 24, 26. The output of sensing module 46 may be received by processor 42. In some cases, processor 42 may apply additional processing to the bioelectrical signals, e.g., convert the output to digital values for processing and/or amplify the bioelectrical brain signal. In addition, in some examples, sensing module 46 or processor 42 may filter the signal from the selected electrodes 24, 26 in order to remove undesirable artifacts from the signal, such as noise from cardiac signals generated within the body of patient 12. Although sensing module 46 is incorporated into a common outer housing with stimulation generator 44 and processor 42 in FIG. 2, in other examples, sensing module 46 is in a separate outer housing from the outer housing of IMD 16 and communicates with processor 42 via wired or wireless communication techniques. In some examples, sensing module 46 may sense brain signals substantially at the same time that IMD 16 delivers therapy to patient 14. In other examples, sensing module 46 may sense brain signals and IMD 16 may deliver therapy at different times.

Memory 40 may include any volatile or non-volatile media, such as a random access memory (RAM), read only memory (ROM), non-volatile RAM (NVRAM), electrically erasable programmable ROM (EEPROM), flash memory, and the like. Memory 40 may store computer-readable instructions that, when executed by processor 42, cause IMD 16 to perform various functions described herein. Memory 40 may be considered, in some examples, a non-transitory computer-readable storage medium comprising instructions that cause one or more processors, such as, e.g., processor 42, to implement one or more of the example techniques described in this disclosure. The term "non-transitory" may indicate that the storage medium is not embodied in a carrier wave or a propagated signal. However, the term "non-transitory" should not be interpreted to mean that memory 40 is non-movable. As one example, memory 40 may be removed from IMD 16, and moved to another device. In certain examples, a non-transitory storage medium may store data that can, over time, change (e.g., in RAM).

In the example shown in FIG. 2, processor 42 controls switch module 48 to sense bioelectrical brain signals with selected combinations of electrodes 24, 26. In particular, switch module 48 may create or cut off electrical connections between sensing module 46 and selected electrodes 24, 26 in order to selectively sense bioelectrical brain signals, e.g., in particular portions of brain 28 of patient 12. Processor 42 may also control switch module 48 to apply stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 22A, 22B and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48. In some examples, IMD 16 may include separate current sources and sinks for each individual electrode (e.g., instead of a single stimulation generator) such that switch module 48 may not be necessary.

Stimulation generator 44 may be a single channel or multi-channel stimulation generator. For example, stimulation generator 44 may be capable of delivering, a single stimulation pulse, multiple stimulation pulses or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Telemetry module 50 may support wireless communication between IMD 16 and an external programmer 14 or another computing device under the control of processor 42. Telemetry module 50 in IMD 16, as well as telemetry modules in other devices and systems described herein, such as programmer 14, may accomplish communication by radiofrequency (RF) communication techniques. In addition, telemetry module 50 may communicate with external programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
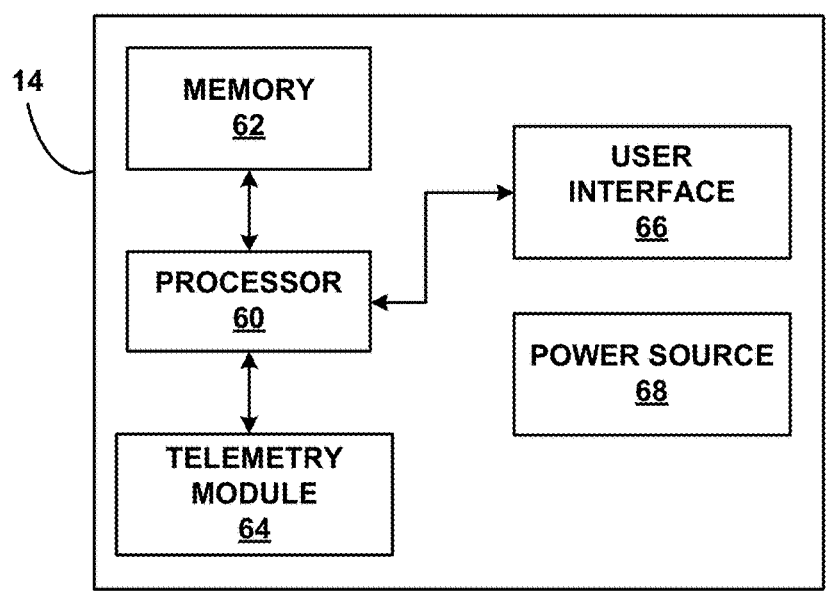
FIG. 3 is a conceptual diagram illustrating an example medical device programmer.

FIG. 3 is a conceptual block diagram of an example external medical device programmer 14, which includes processor 60, memory 62, telemetry module 64, user interface 66, and power source 68. Processor 60 controls user interface 66 and telemetry module 64, and stores and retrieves information and instructions to and from memory 62. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

Memory 62 may include instructions for operating user interface 66 and telemetry module 64, and for managing power source 68. Memory 62 may also store any therapy data retrieved from IMD 16 during the course of therapy. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Memory 62 may be considered, in some examples, a non-transitory computer-readable storage medium comprising instructions that cause one or more processors, such as, e.g., processor 60, to implement one or more of the example techniques described in this disclosure. The term "non-transitory" may indicate that the storage medium is not embodied in a carrier wave or a propagated signal. However, the term "non-transitory" should not be interpreted to mean that memory 62 is non-movable. As one example, memory 62 may be removed from programmer 14, and moved to another device. In certain examples, a non-transitory storage medium may store data that can, over time, change (e.g., in RAM).

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 may deliver operating power to the components of programmer 14 Power source 68 may include a battery and a power generation circuit to produce the operating power. In some examples, the battery may be rechargeable to allow extended operation.

Figure 4:
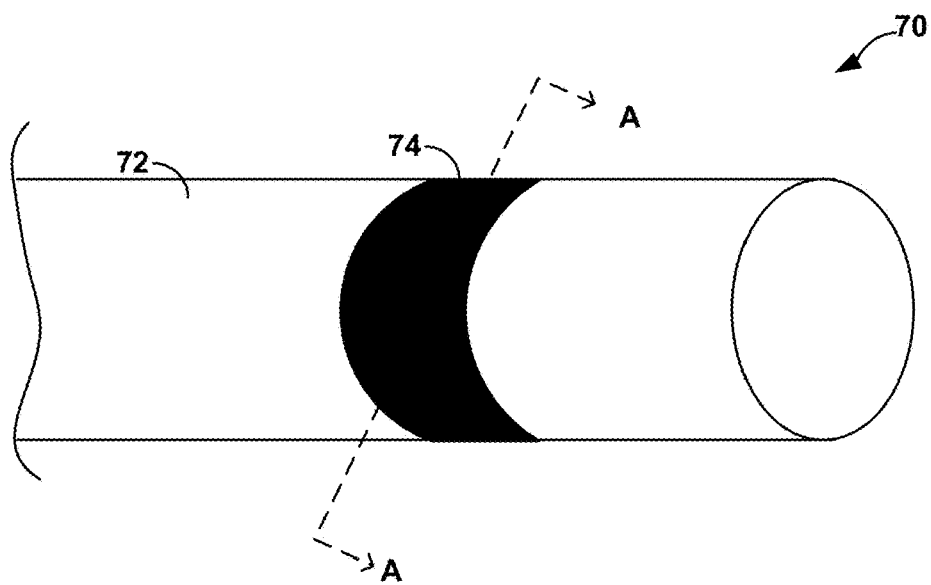
FIG. 4 is a conceptual diagram illustrating an example medical device lead.

FIG. 4 is a conceptual diagram illustrating an example medical device lead 70 for use in a medical device system, such as, e.g., medical device system 10 of FIG. 1. Lead 70 may be substantially the same or similar to that of lead 20A or 20B of FIG. 1. For ease of description, lead 70 will be described with regard to system 10 of FIG. 1. As shown, lead 70 includes a single ring electrode 74 located on lead body 72. Lead body 72 is formed of an electrically insulating, biocompatible material, such as, e.g., polyurethane or silicone. Lead body 72 includes a lead wire (not shown in FIG. 4) which runs the length of lead body 72 and electrically couples electrode 74 to IMD 16 for delivery of electrical stimulation and/or sensing of electrical signals as described herein.

Figure 5:
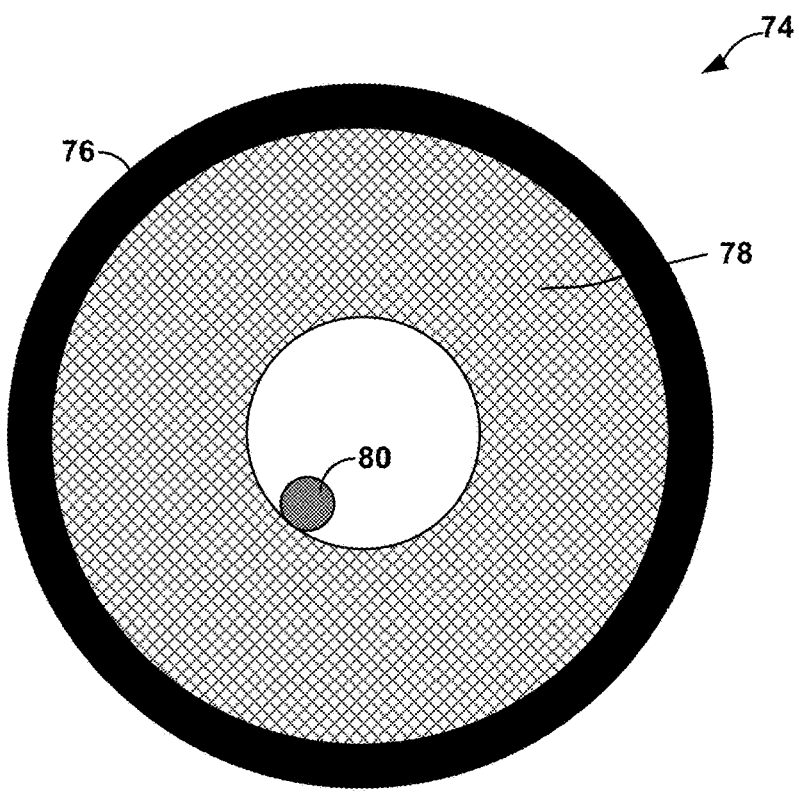
FIG. 5 is a conceptual diagram illustrating the example medical device lead of FIG. 4 along cross-section A-A.

FIG. 5 is a conceptual diagram illustrating the example medical device lead of FIG. 4 along cross-section A-A. As shown, electrode 74 includes electrode substrate 78 and coating 76 deposited on the outer surface of substrate 78. Conversely, the inner surface of substrate 78 is mechanically and electrically coupled to conductive lead wire 80. When implanted in patient 12, the outer surface of coating 76 on electrode substrate 78 may interface or be in contact with tissue of patient 12. Electrical stimulation may be delivered to patient 12 via electrode 74 by conducting electrical stimulation generating by IMD 16 from lead wire 80 across coating 76 via electrode substrate 78. Likewise, for sensing with electrode 74, electrical signals may be transmitted across coating 76 to lead wire 80 via substrate 78 to IMD 16.

As noted above, lead wire 80 may be formed of a composition including titanium or alloys thereof, such as, e.g., Ti-15Mo or other low modulus beta titanium alloys, which have high electrical resistance to reduce heating of tissue adjacent to electrodes during MRI scanning, e. g., as compared to that of Pt, Pt—Ir, or MR35 lead wires. Additionally, as noted above, Ti and Ti alloys, and Ti-15Mo alloys in particular, may exhibit superior fatigue life, e.g., as compared to that of Pt or Pt—Ir lead wires. In some instances, lead wire 80 may be formed of titanium or alloys thereof, where lead wire 80 exhibits a wire resistivity greater than approximately 80 $\mu\Omega$-cm. Example alloying elements may include one or a combination of Mo, Nb, Ta, Zr, Fe, Sn, Fe and Al. In one example, lead wire 80 may consist essentially of titanium or titanium alloy, where any additionally material in present only in an amount that does not alter one or more properties of the material in a manner that does not allow lead wire 80 to function as described herein.

As noted above, in some examples, it may be desirable for electrode substrate 80 to be formed of a composition other than that of Pt or alloys thereof, such, as, e.g., Pt—Ir. In particular, substrate 78 of electrode 74 may be formed of one or more of titanium, tantalum, niobium, and alloys thereof, such as, e.g., Ti15Mo to allow for conduction of electrical signals from lead wire 80 as well as allowing for substrate 78 to be welded, e.g., laser welded, to lead wire 80. Example titanium materials for forming substrate 78 include commercially pure titanium grade 1, 2, 3, and 4 and any other biocompatible Ti alloys. In some examples, substrate 78 may be formed of Ti—Mo alloy, e.g., wherein Mo is present in between about 5 wt % to about 25 wt %. Other example alloying elements may include Nb, Ta, Zr, Sn, Fe and Al. In some examples, substrate 78 may have substantially the same composition of that of lead wire 80. In one example, substrate is formed on MP35. In one example, substrate 78 may consist essentially of Ti, where any additionally material in present only in an amount that does not alter one or more properties of the material in a manner that does not allow substrate 78 to function as described herein.

While the use of one or more of titanium, tantalum, niobium, and alloys thereof to form substrate 78 may provide for one or more benefits, as noted above, in some examples, Ti and Ti alloys may have a relatively low charge density limits compared to that of Pt based alloys, which may decrease the effectiveness for delivering electrical stimulation. In accordance with one of aspects of this disclosure, coating 76 may be applied to outer surface of electrode substrate 78. The coating of composition may increase the charge density of electrode 74 by increasing the surface roughness along with providing a fractal morphology that results in large increase effective surface area compared to that of the surface of electrode substrate 78. Also, the combination of electrode substrate 78 and coating may provide for a reduced electrode impedance compared to that of Pt-10Ir electrodes. In some cases, tower over impedance will reduce energy consumption and increase device life.

Coating 76 on substrate 78 may be formed of a composition comprising at least one of Pt, TiN, IrOx, and PDOT. For examples utilizing Pt coatings, the composition of coating 76 may be substantially all Pt or alloyed with one or more elements, such as, e.g., Ir, Rh, and Au. For examples utilizing TiN coatings, the composition of coating 76 may include any suitable ratio of Ti to N, e.g., a ratio of approximately 1:1. Coating 76 may have a composition that provide for a relatively large increase in the effective surface roughness and effective surface area compared to that of the uncoated electrode substrate surface. In one example, coating 76 may consist essentially of one or more of Pt, TiN, IrOx, and PDOT, where any additionally material in present only in an amount that does not alter one or more properties of the material in a manner that does not allow coating 76 to function as described herein.

Surface coating 76 may be deposited on the outer surface of substrate 78 to define any suitable thickness over substrate. For example, coating 76 may have a thickness between approximately 0.5 micrometers and approximately 15 micrometers. Coating 76 may have a substantially uniform thickness over the surface of substrate 78 or, alternatively, may vary in thickness. In some examples, coating 76 may cover substantially the entire exposed outer surface of substrate 78.

Any suitable technique may be used to form coating 76 on substrate 78. For example, coating 76 may be deposited using sputtering, such as, e.g., vacuum sputtering, PVD, CVD, or plasma enhanced deposition process when the composition of coating 76 includes one or more of Pt, TiN, or IrOx. As another example, when coating 76 is formed of conductive PDOT, electropolymerization techniques may be used.

Figure 26A:
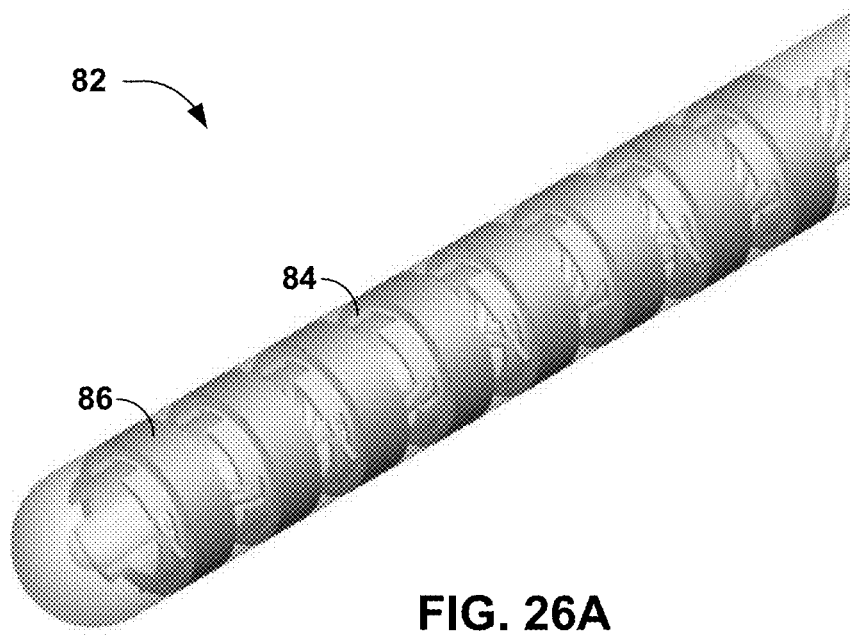
FIGS. 26A-C are schematic diagrams illustrating another example medical device lead.
Figure 26B:
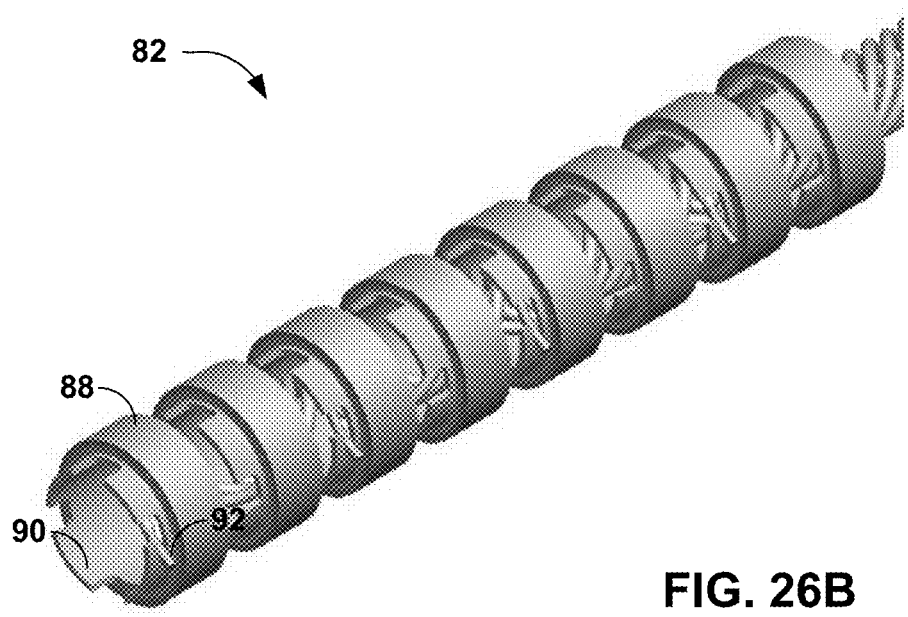
Figure 26C:
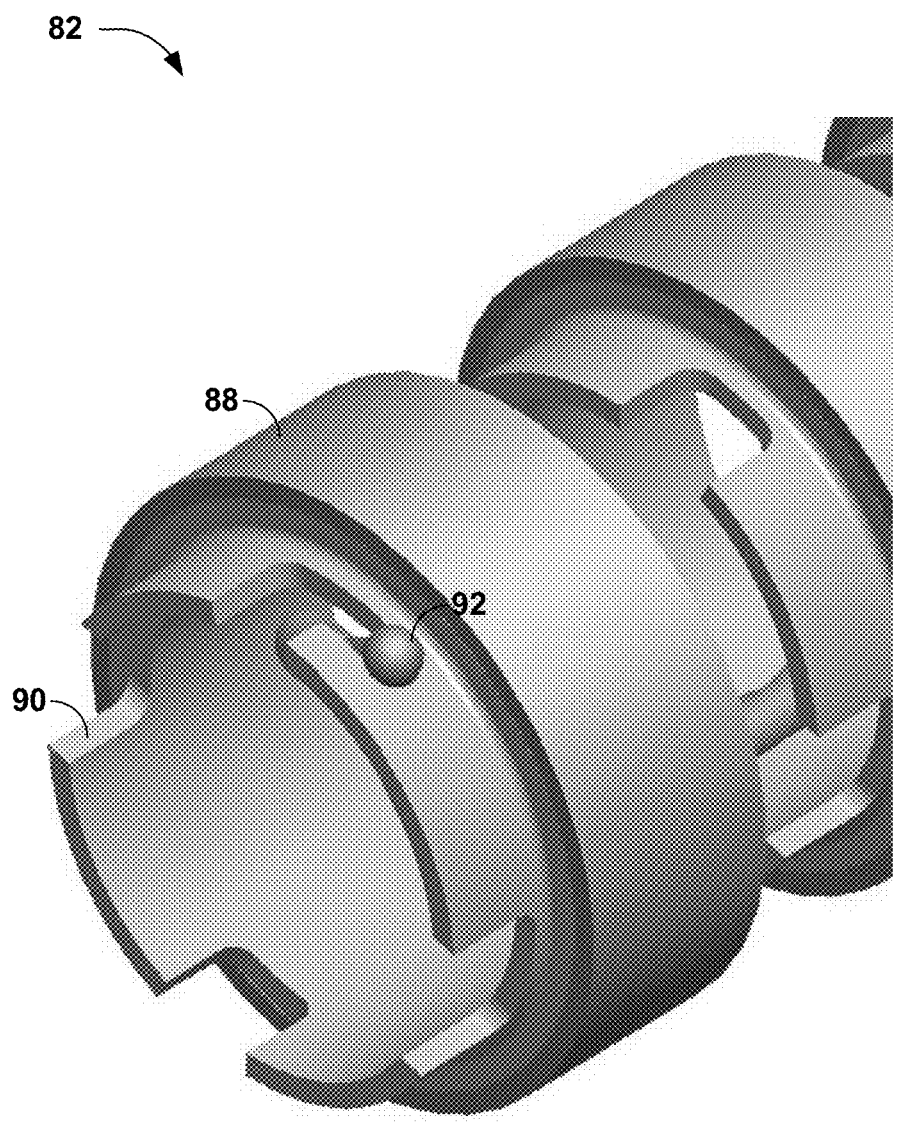

FIGS. 26A-C are schematic diagrams illustrating another example medical device lead 82. Lead 82 includes a plurality of rings electrodes, including electrode 86 located at the end of the distal section 84 of lead 82. Electrode 86 may be substantially the same or similar to that of electrode 74 of lead 70 described previously.

FIG. 26B illustrates the distal end of lead 82. As shown, electrode 74 includes electrode substrate 90 with the outer surface coated with coating 88. One of the plurality of lead wires of lead 82, lead wire 92, is welded or otherwise coupled to substrate 90. Substrate 90, coating 88, and lead wire 92 may be substantially similar to that of substrate 78, coating 76, and lead wire 80 of lead 70 described previously.

FIG. 26C is a magnified view of lead 82 showing distal electrode 88. As shown, electrode substrate 90 exhibits a stepped configuration with respect to the bumped surface formed by the welding of lead wire 92 to substrate 90. In this manner, the weld bump does not protrude from the smooth circular cross section of the distal end of lead 82 after the lead body has been overmolded.

Although examples of the present disclosure have primarily been described with regard to coated ring electrodes, examples are not limited as such. For example, in some cases a lead may include one or more segmented electrodes. The segments electrodes may each include an electrode substrate coupled (e.g., welded) to a lead wire having those compositions described herein. The outer surface of the electrode substrate for each of the segmented electrodes may be coated with those compositions described herein.

As another example, examples of the disclosure may include paddle leads having any suitable shape and configuration. In some examples, each electrode located on the lead may include an electrode substrate coupled (e.g., welded) to a lead wire having those compositions described herein. The outer surface of the electrode substrate for each of the segmented electrodes may be coated with those compositions described herein. In other examples, rather than including an electrode substrate, the outer surface of lead wire may be coated with those compositions described herein, e.g., after the lead wire has been crimped or otherwise modified in a suitable manner.

EXAMPLES

As series of experiments were performed to evaluate one or more aspects related to the present disclosure. In one instance, a series of Ti rods having a diameter of approximately 0.05 inches were coating with various coatings compositions and various thickness via vacuum sputtering. The properties of the sample coated Ti rods were then evaluated. The below table summarizes the samples that were evaluated.

| Substrate (approx. 0.05"diameter) | Coating Composition | Thickness (approx.) | Application | FIGS. |
|---|---|---|---|---|
| Ti—15Mo rod | Pt | 2 μm | Vacuum sputter coated | 6A-6E |
| Ti—15Mo rod | Pt | 5 μm | Vacuum sputter coated | 8A-8E |
| Ti—15Mo rod | TiN | 4 μm | Vacuum sputter coated | 10A-10E |
| Ti—15Mo rod | TiN | 8 μm | Vacuum sputter coated | 12A-12E |
| Ti—15Mo rod | IrOx | 1 μm | Vacuum sputter coated | 14A-14E |
| Ti Grade 2 rod | Pt | 2 μm | Vacuum sputter coated | 7A-7E |
| Ti Grade 2 rod | Pt | 5 μm | Vacuum sputter coated | 9A-9E |
| Ti Grade 2 rod | TiN | 4 μm | Vacuum sputter coated | 11A-11E |
| Ti Grade 2 rod | TiN | 8 μm | Vacuum sputter coated | 13A-13E |
| Ti Grade 2 rod | IrOx | 1 μm | Vacuum sputter coated | 15A-15E |

Figure 6A:
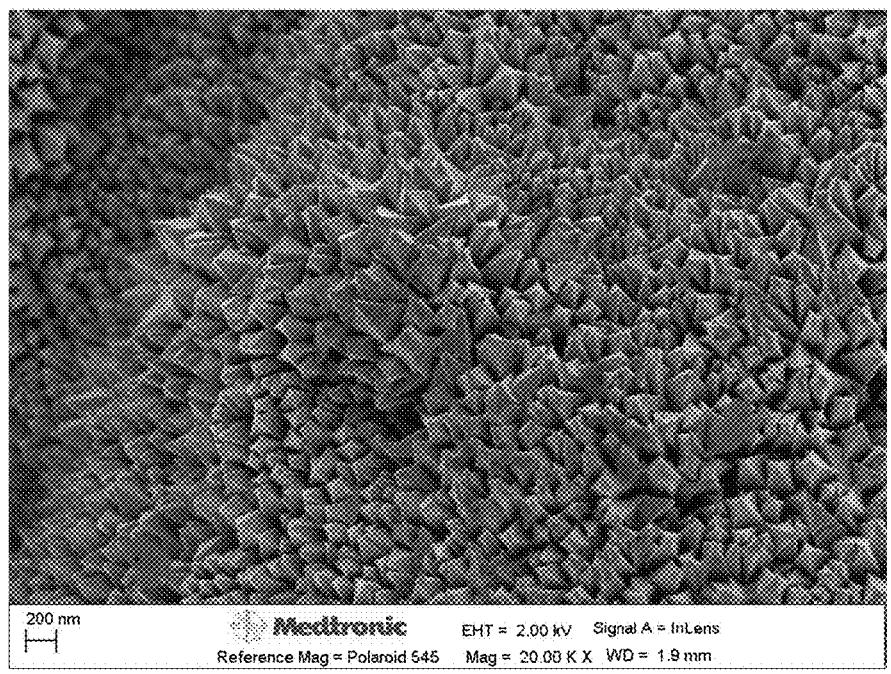
FIGS. 6A-6E, 7A-7E, 8A-8E, 9A-9E, 10A-10E, 11A-11E, 12A-12E, 13A-13E, 14A-14E, 15A-15E, and 16-25 are various images and plots relating to experiments carried out to evaluate one or more aspects of examples of the disclosure.
Figure 6B:
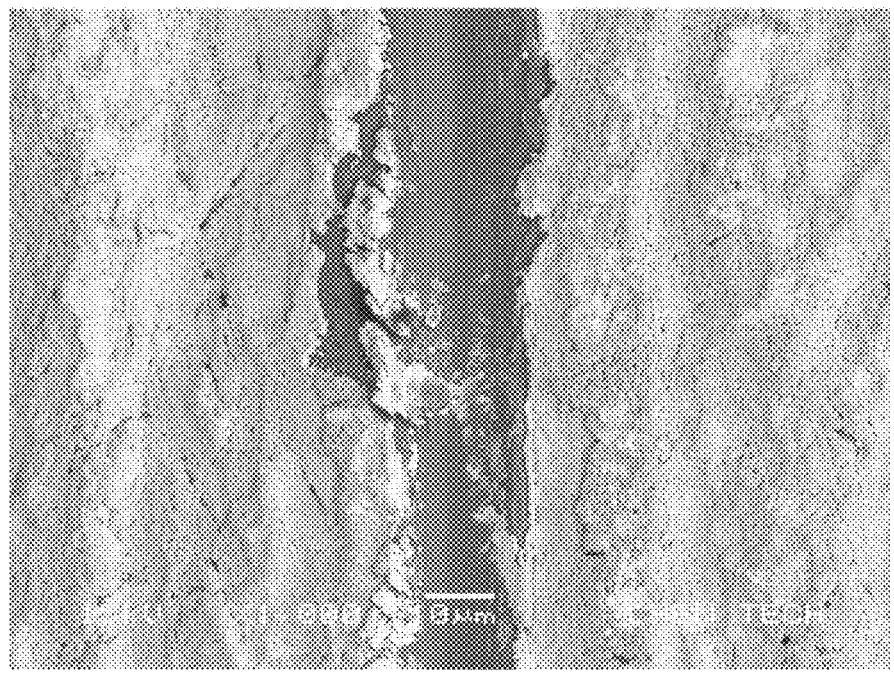
Figure 6C:
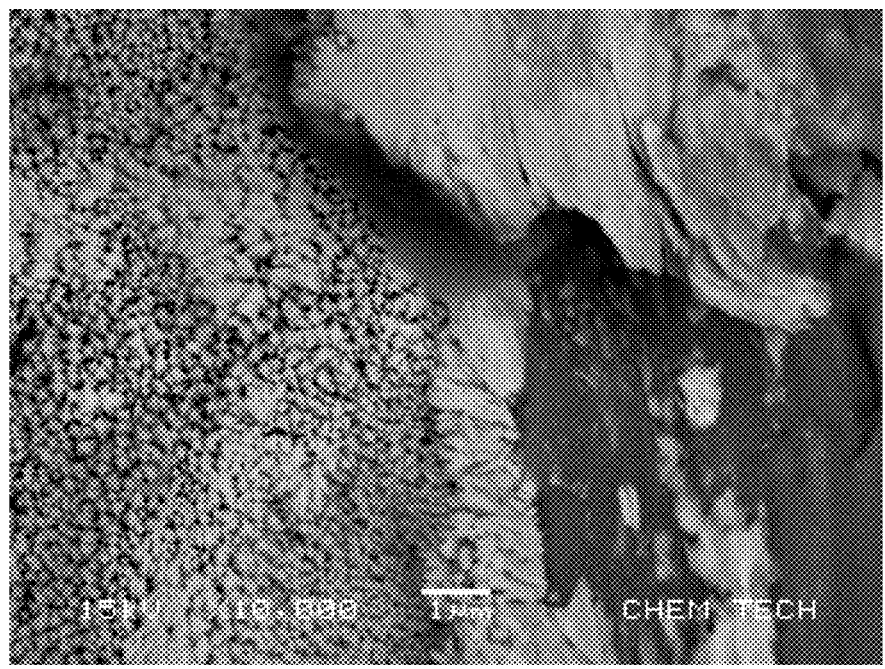
Figure 6D:
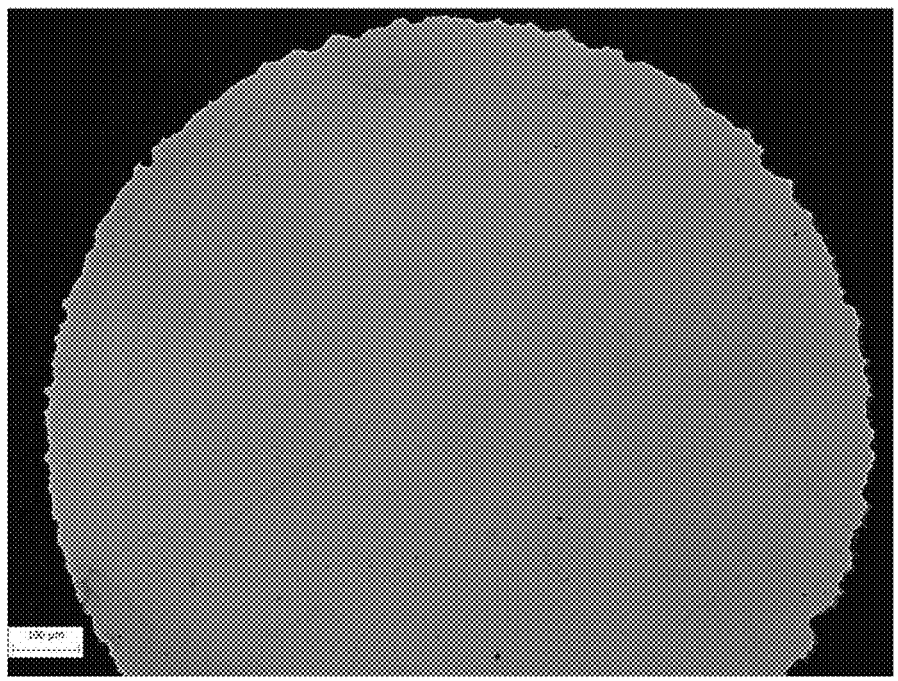
Figure 6E:
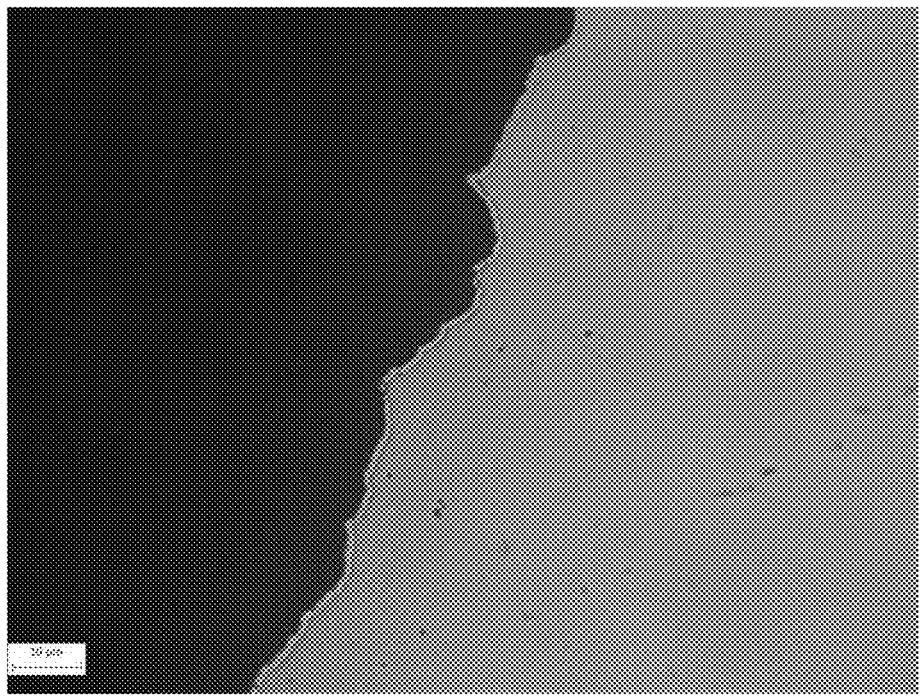
Figure 7A:
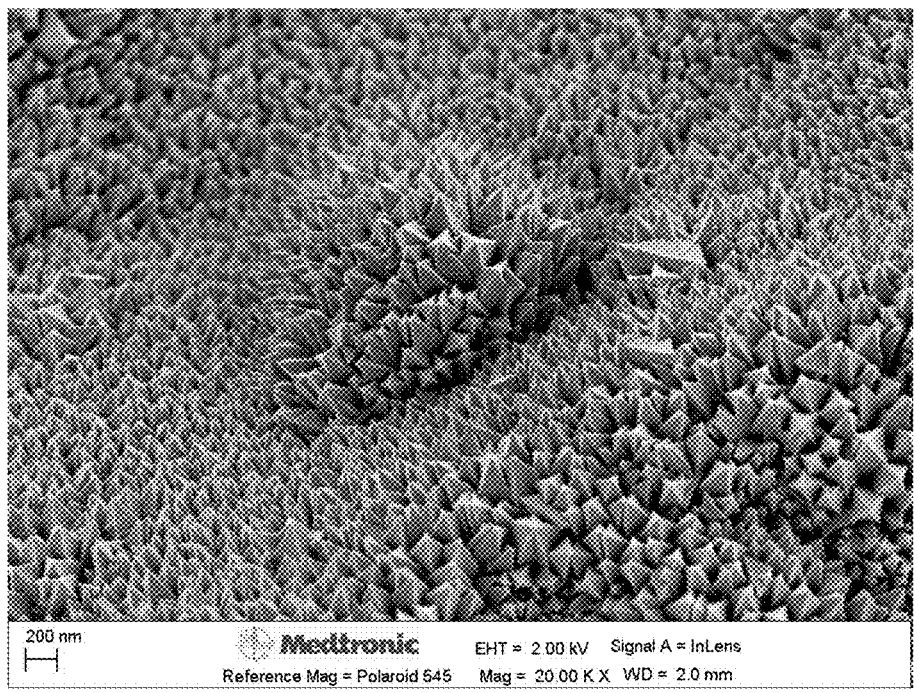
Figure 7B:
Figure 7C:
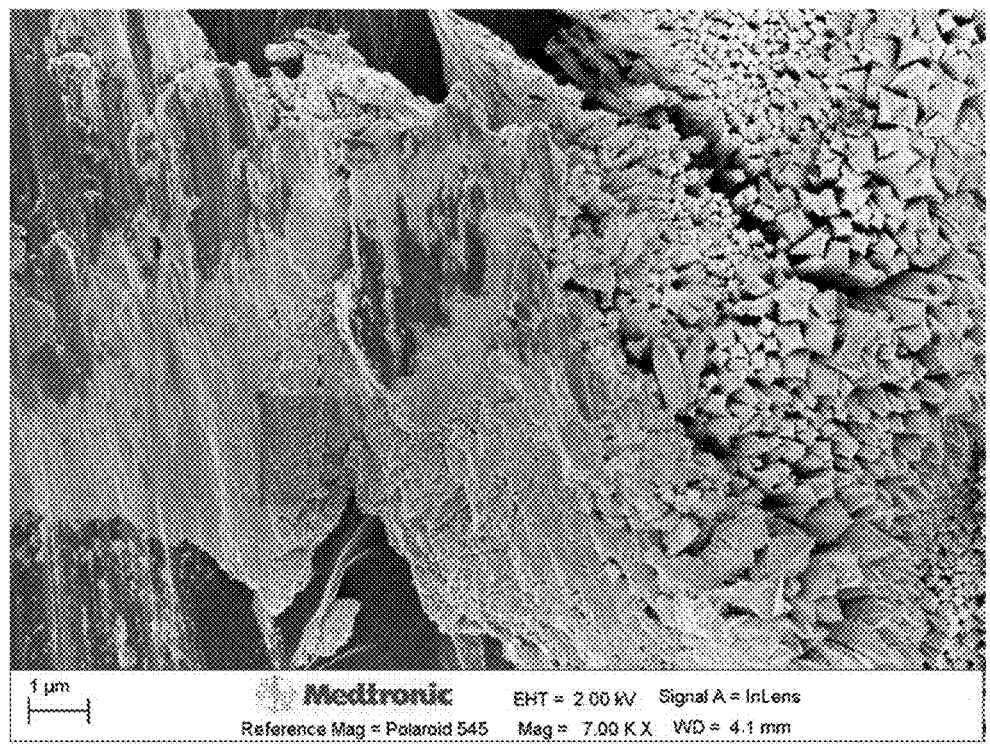
Figure 7D:
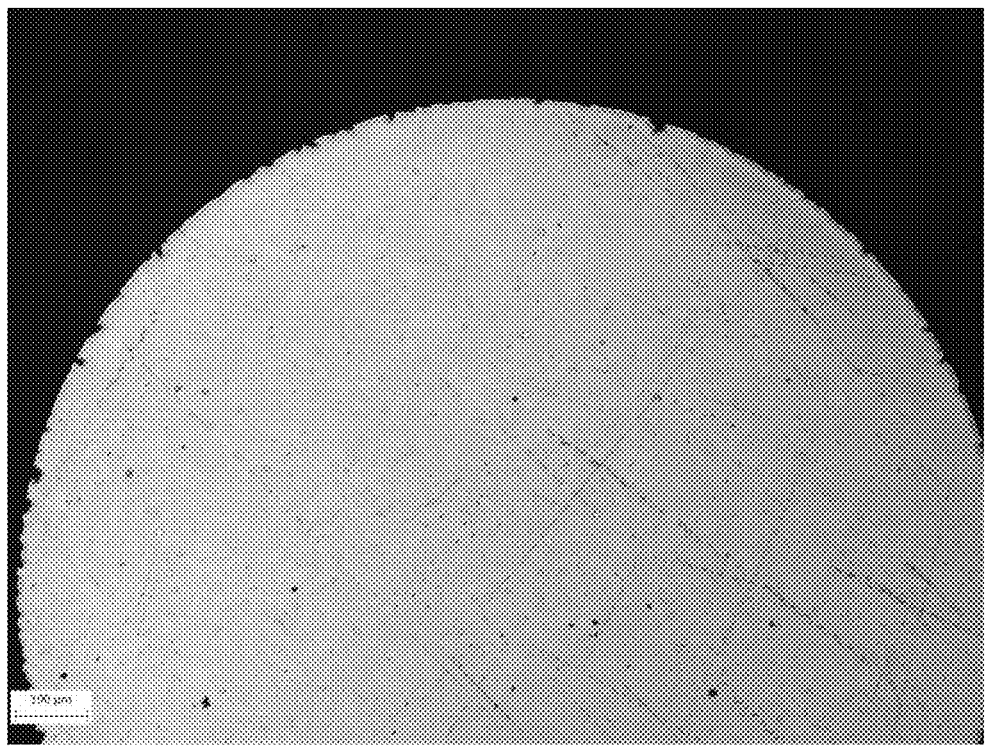
Figure 7E:
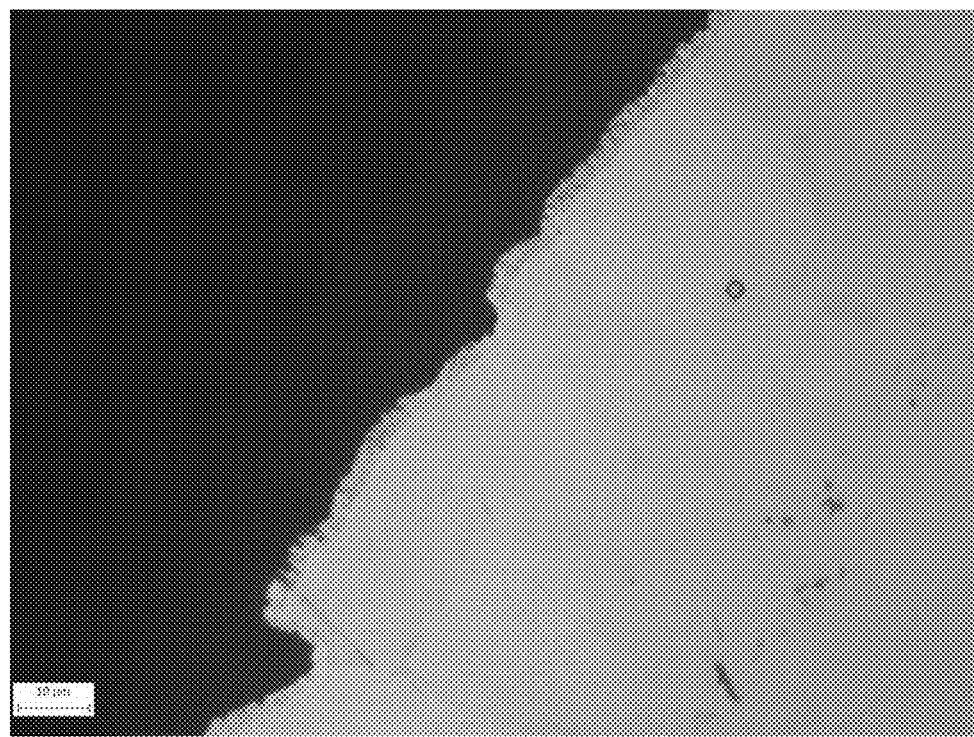
Figure 8A:
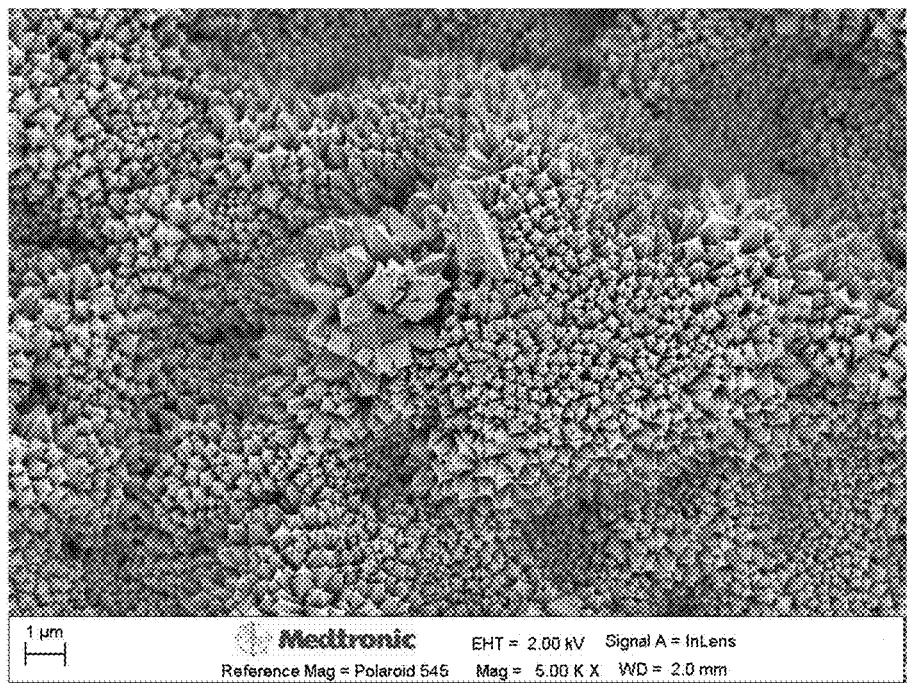
Figure 8B:
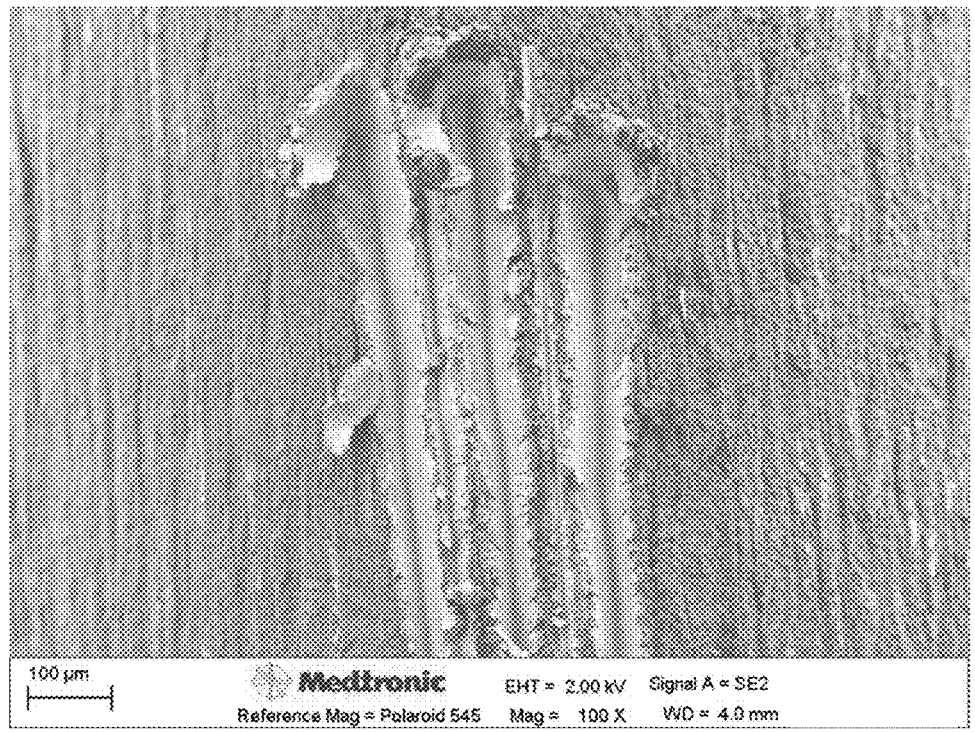
Figure 8C:
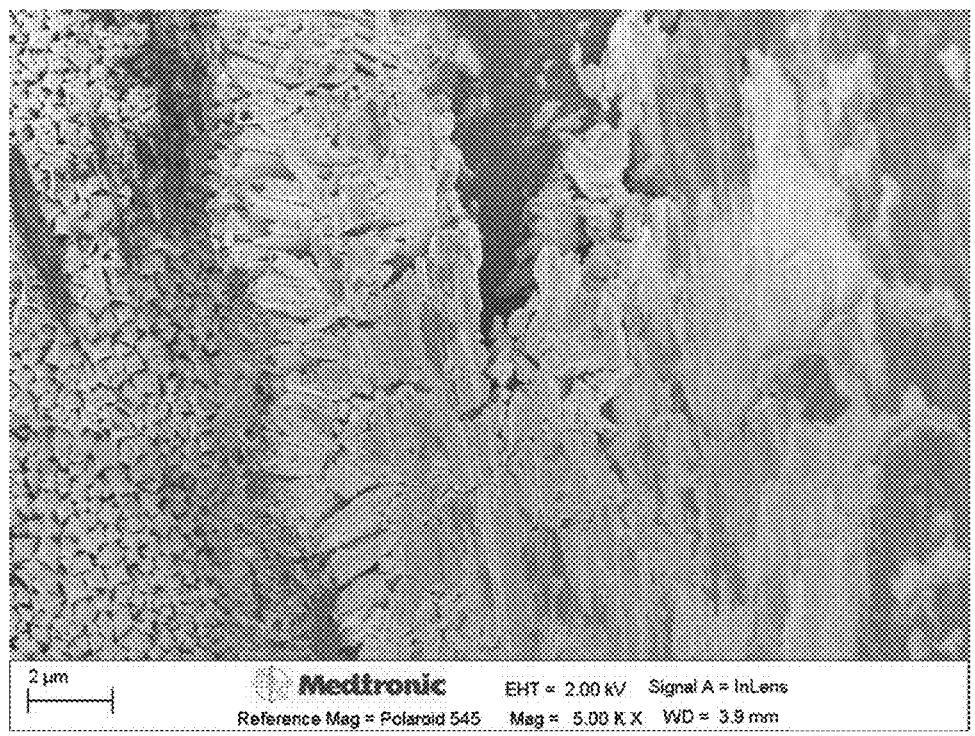
Figure 8D:
Figure 8E:
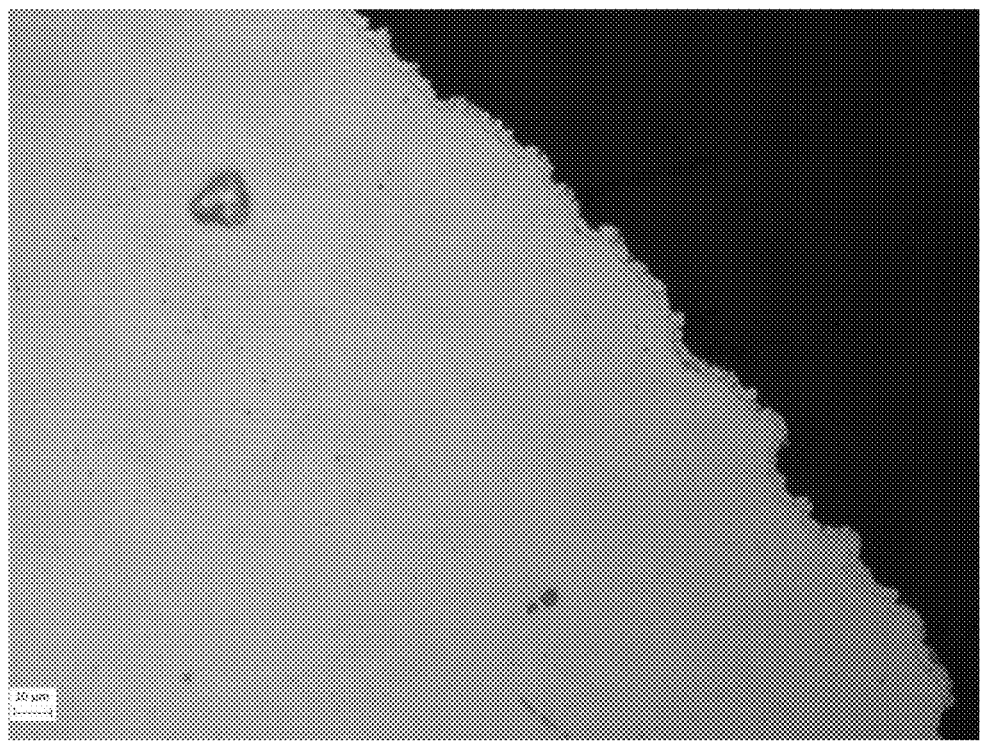
Figure 9A:
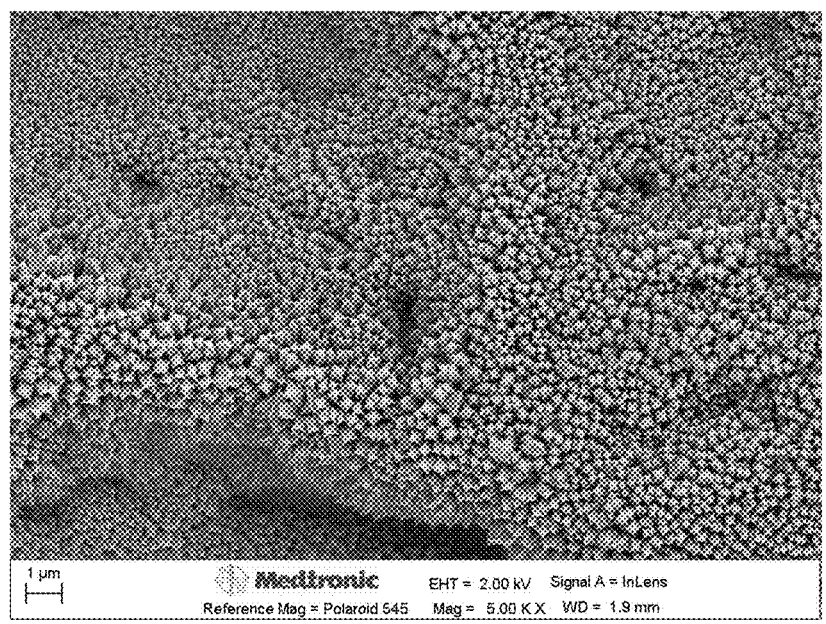
Figure 9B:
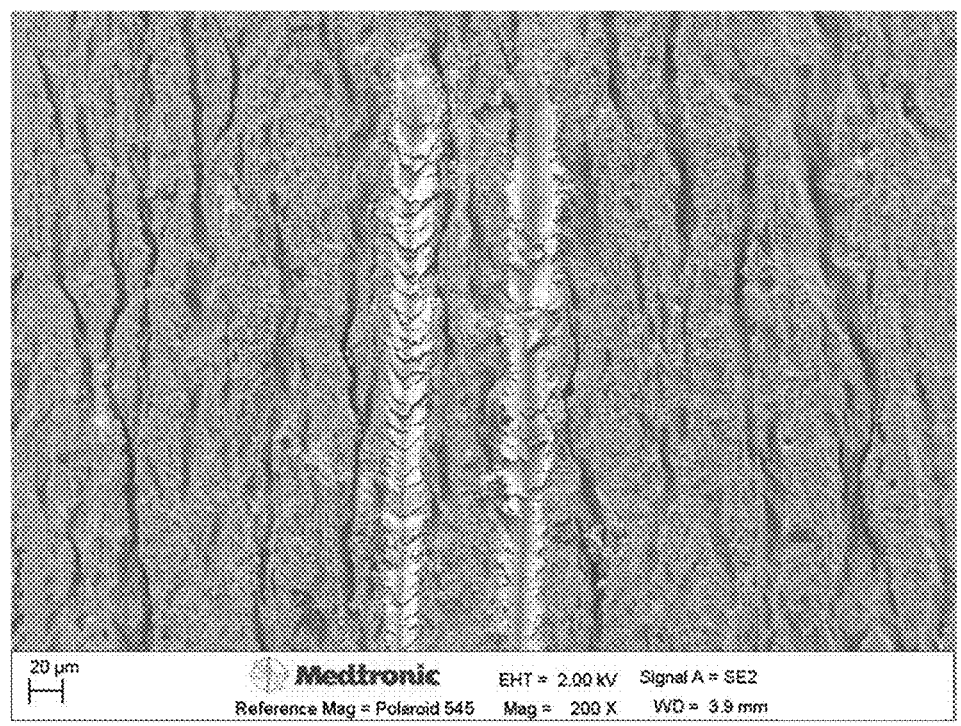
Figure 9C:
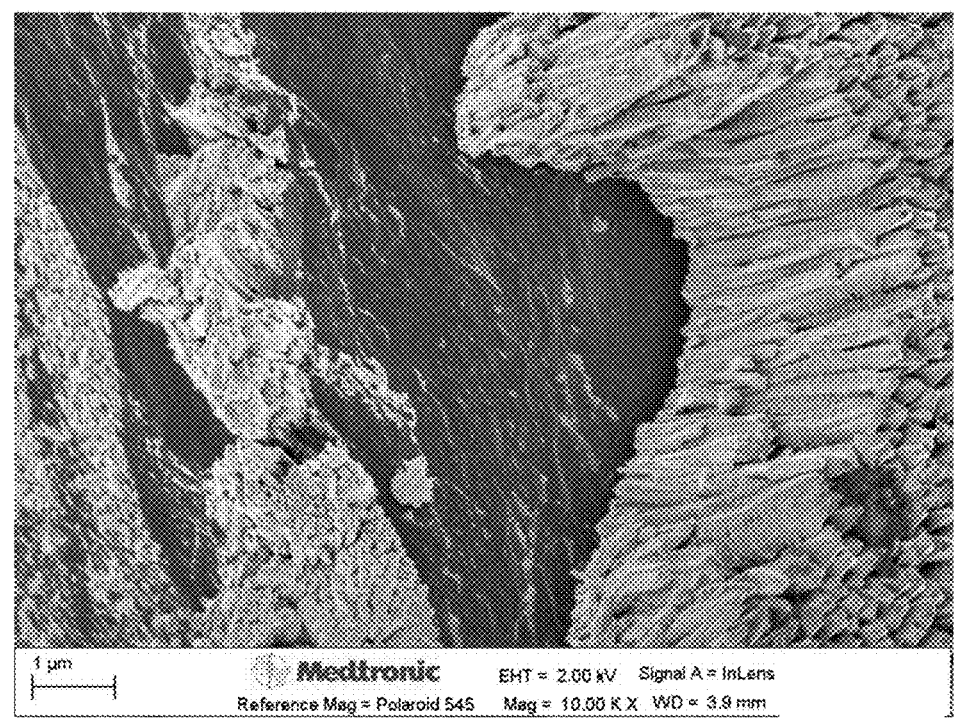
Figure 9D:
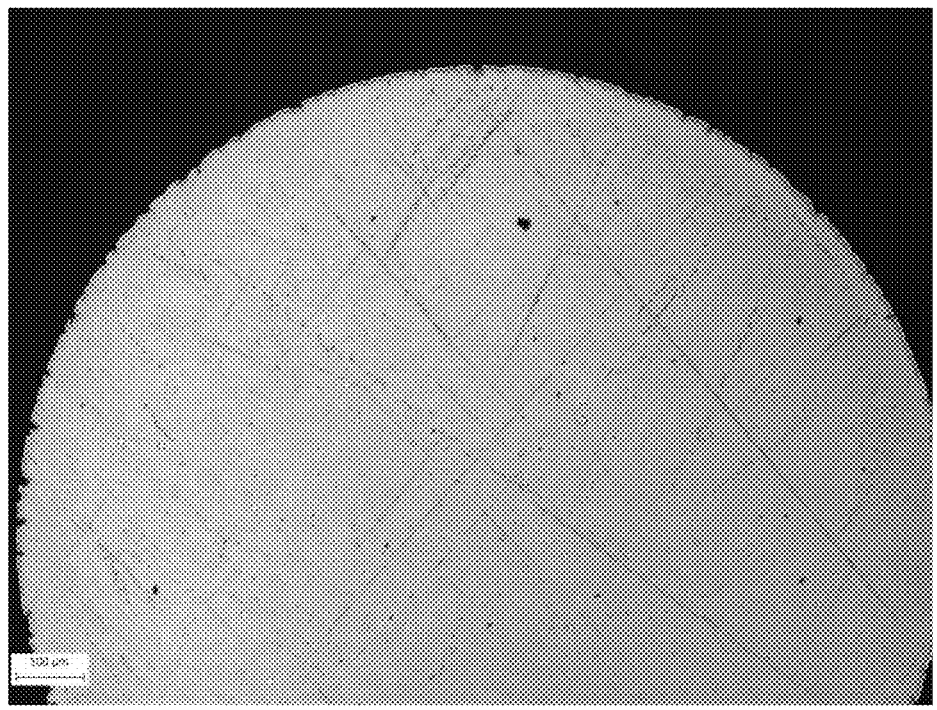
Figure 9E:
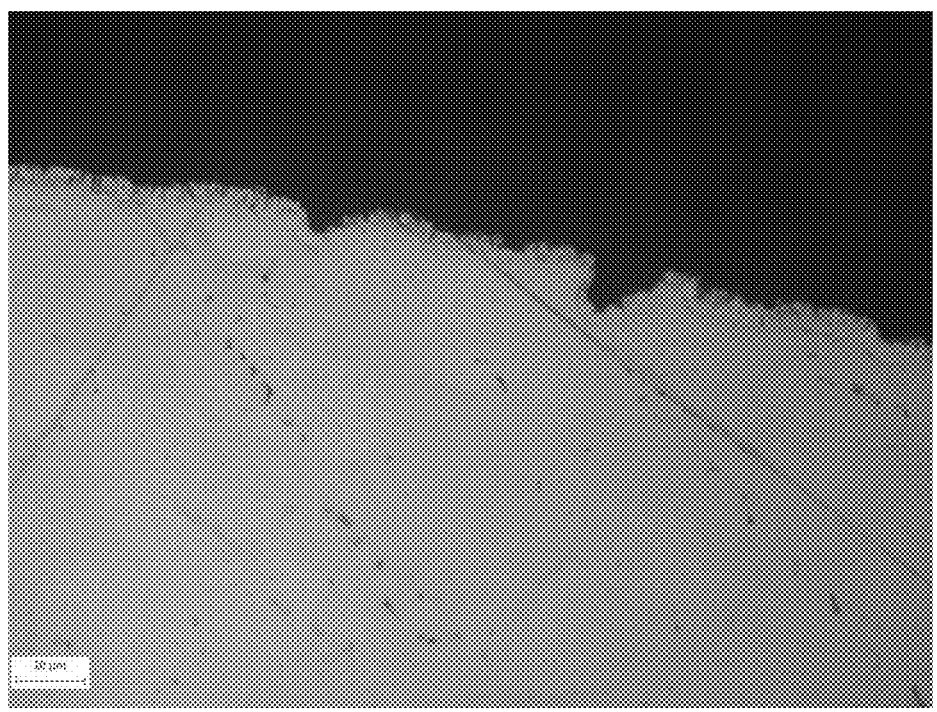
Figure 10A:
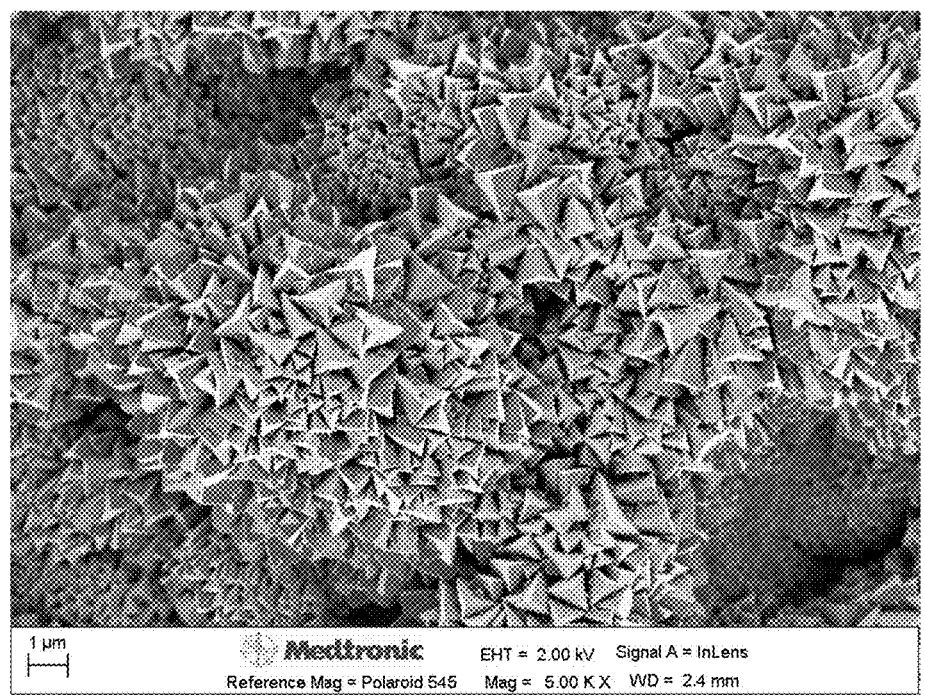
Figure 10B:
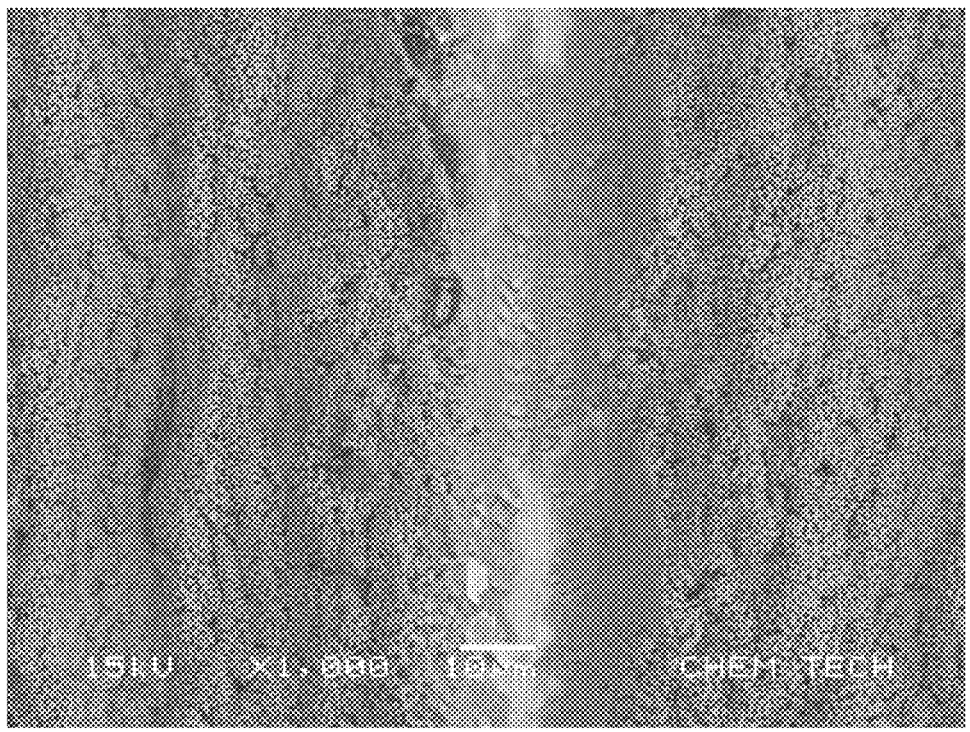
Figure 10C:
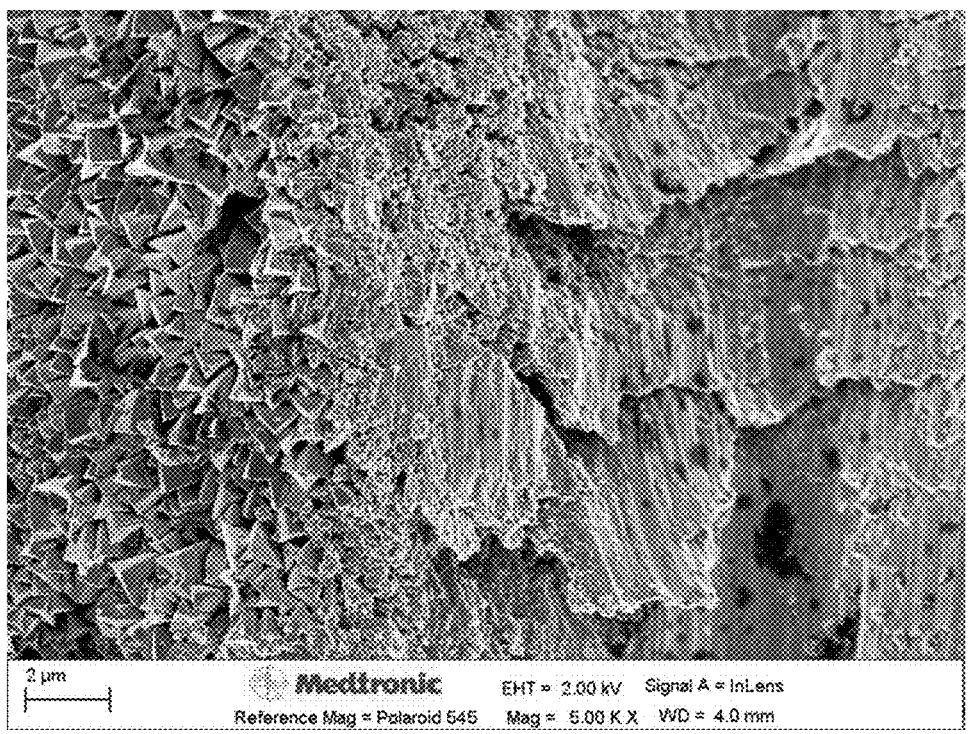
Figure 10D:
Figure 10E:
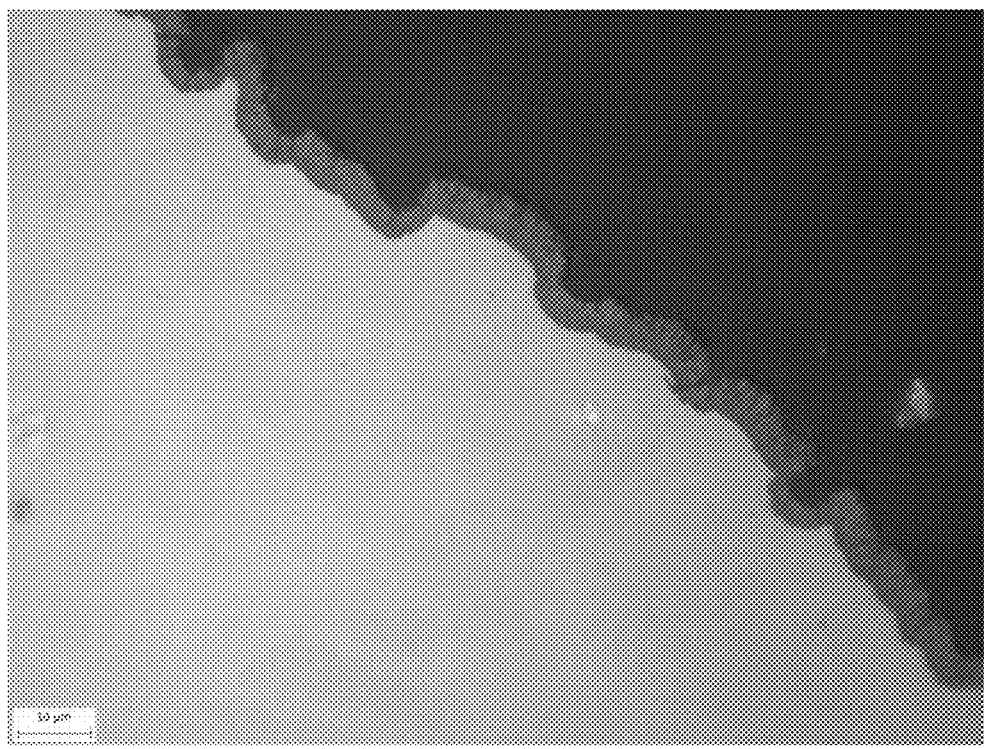
Figure 11A:
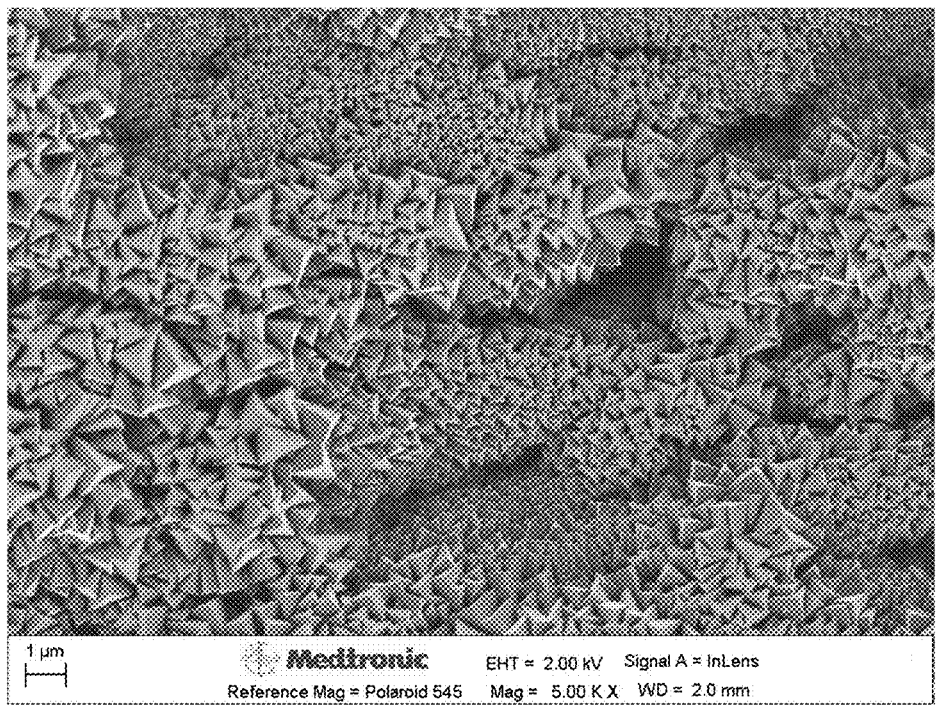
Figure 11B:
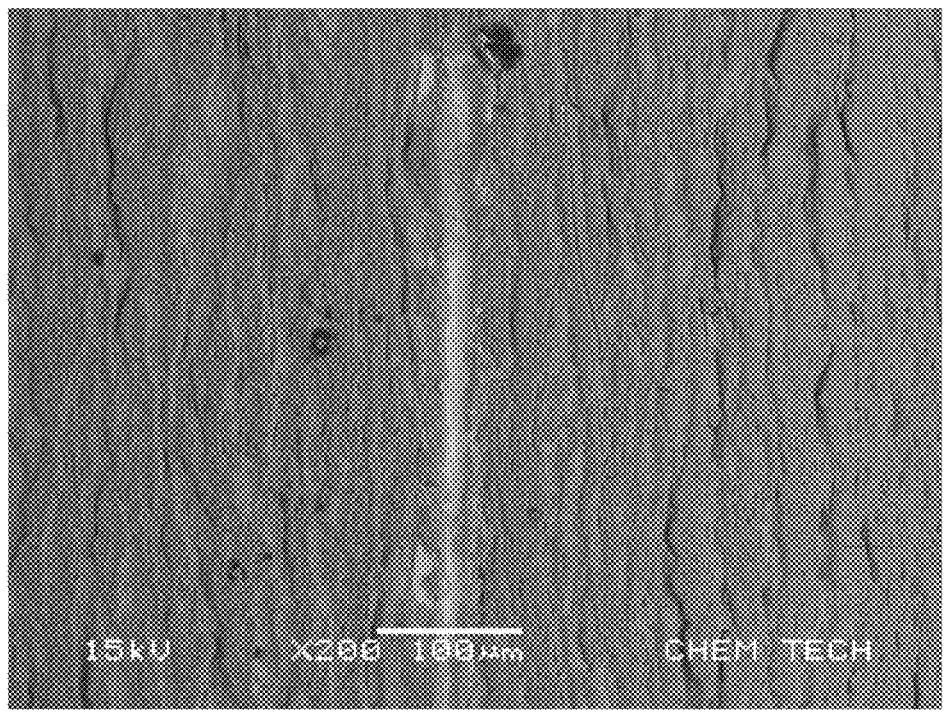
Figure 11C:
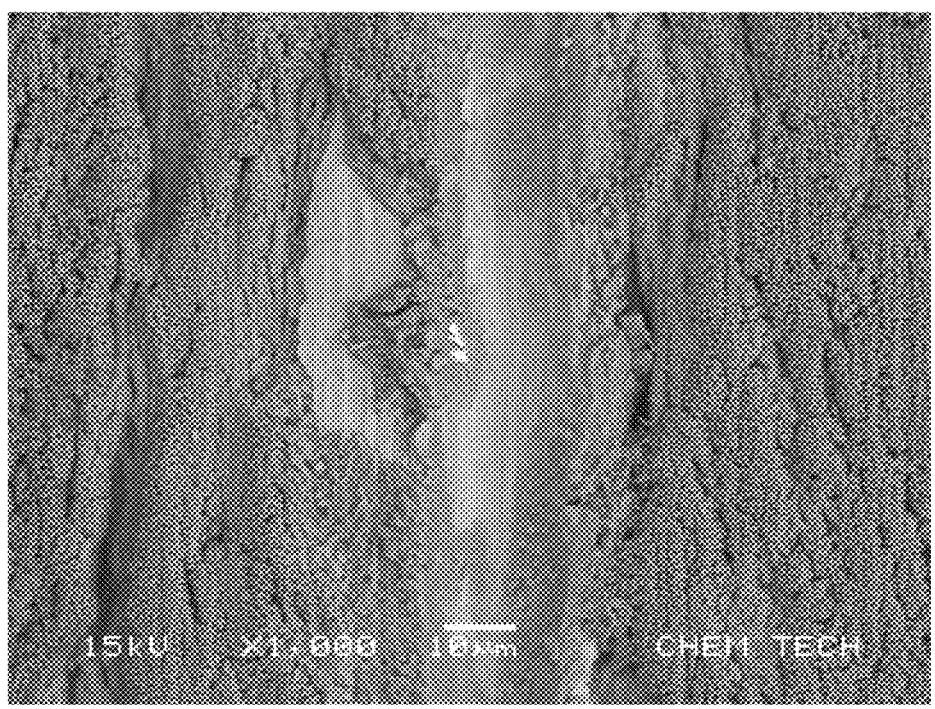
Figure 11D:
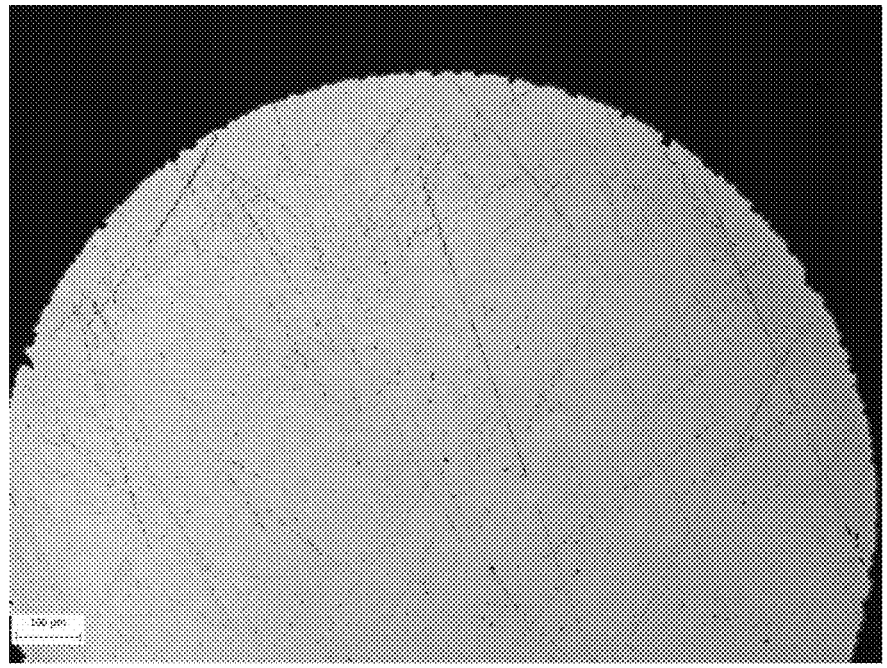
Figure 11E:
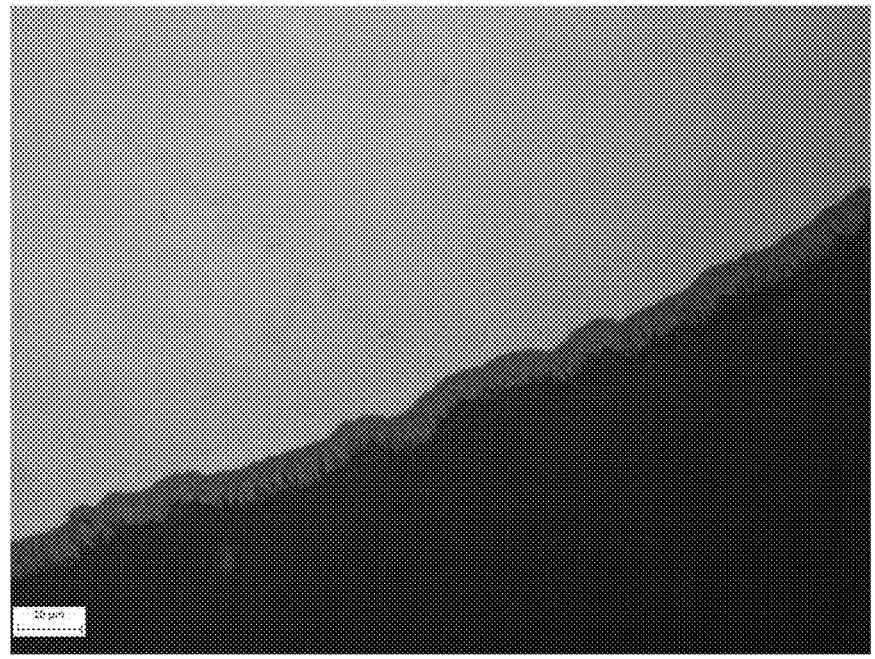
Figure 12A:
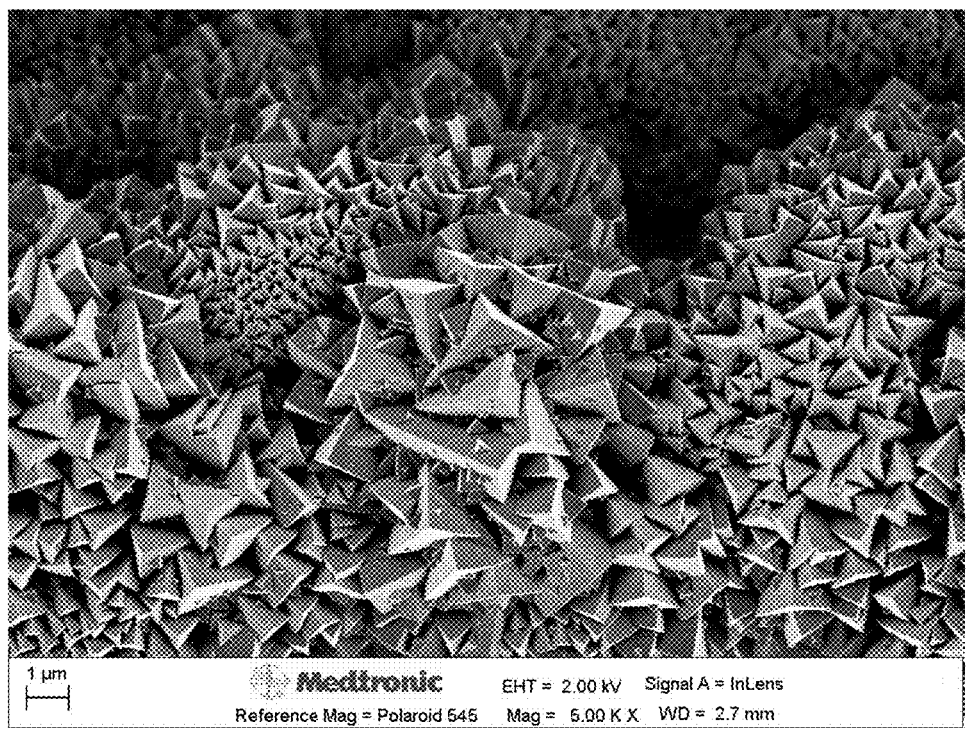
Figure 12B:
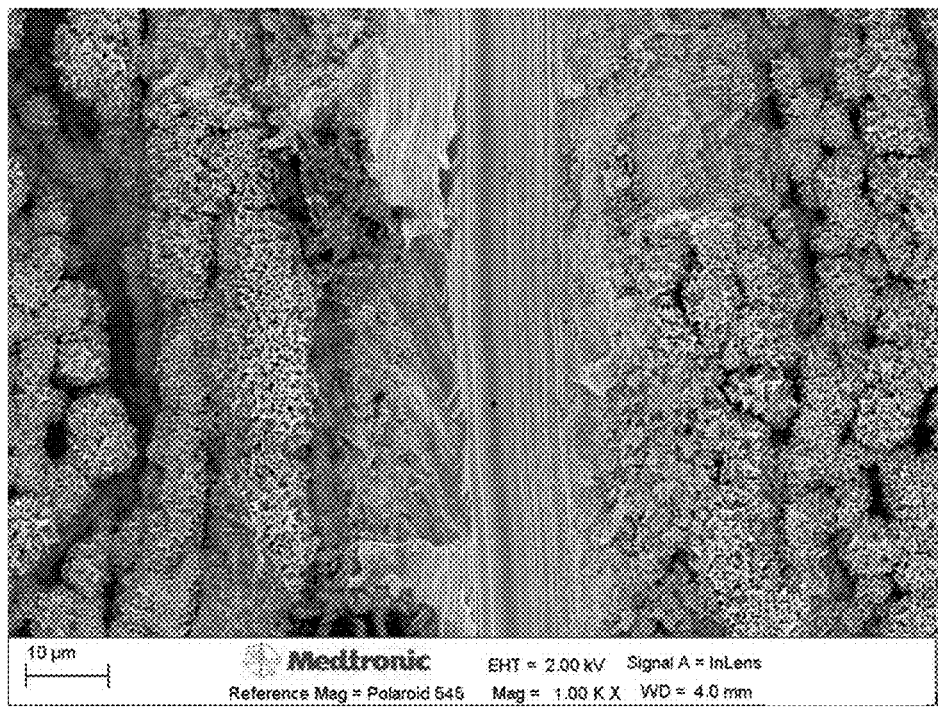
Figure 12C:
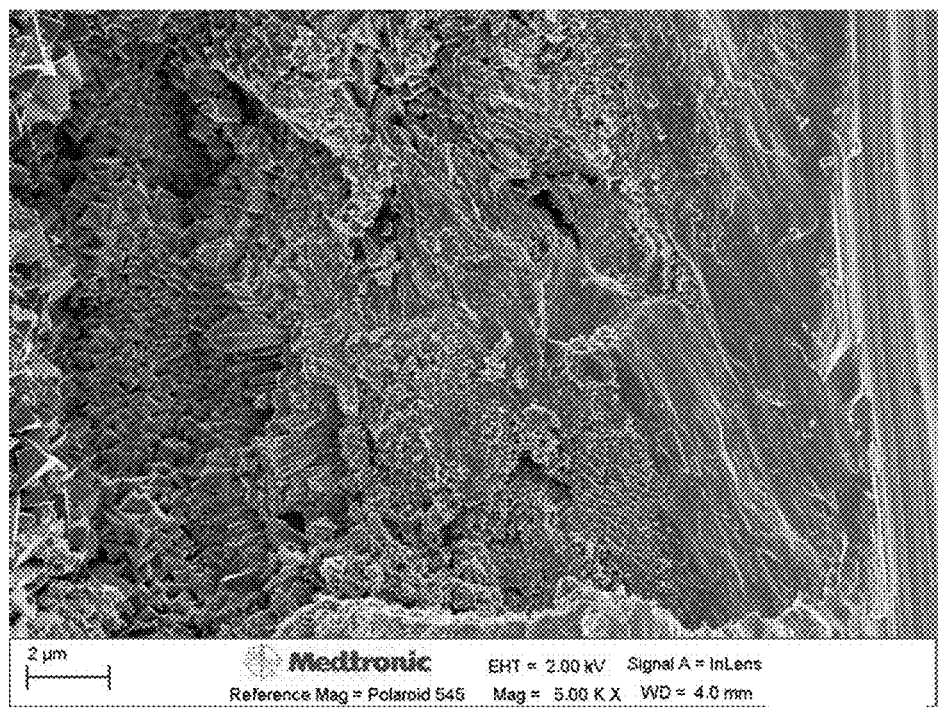
Figure 12D:
Figure 12E:
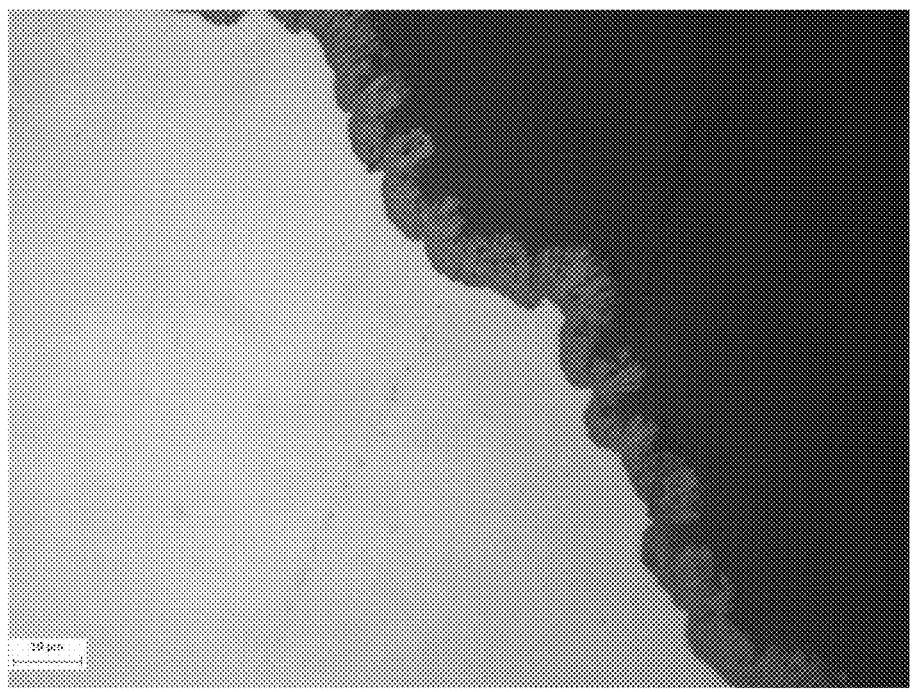
Figure 13A:
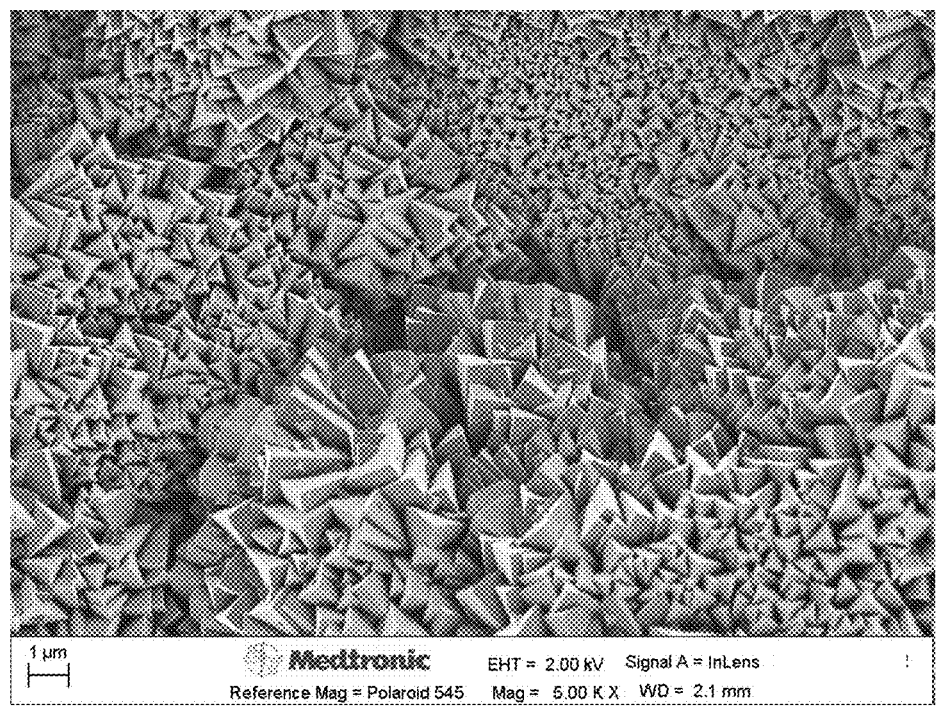
Figure 13B:
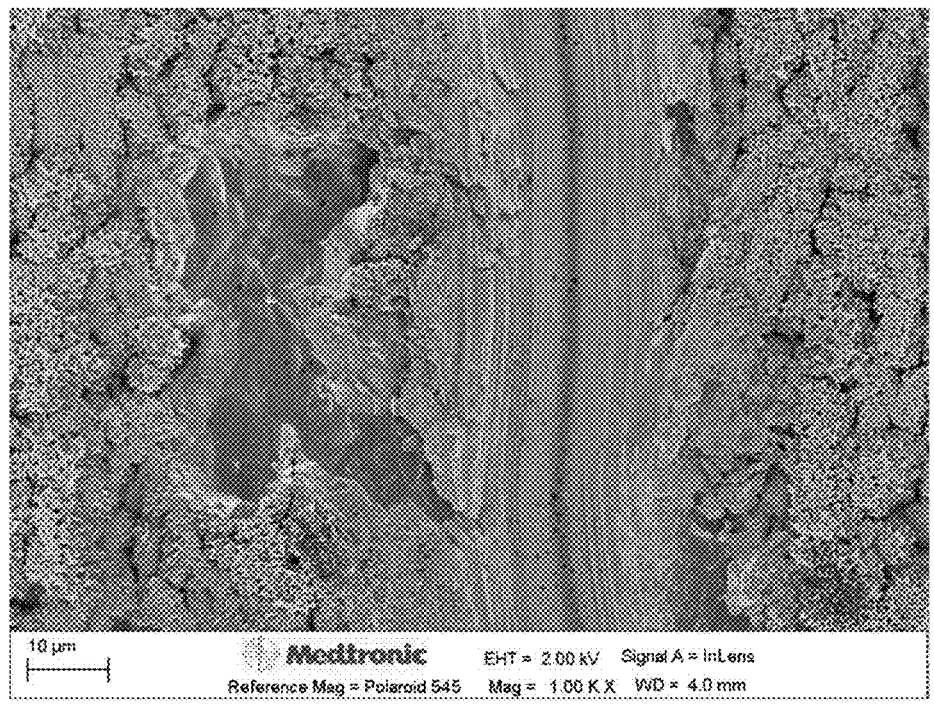
Figure 13C:
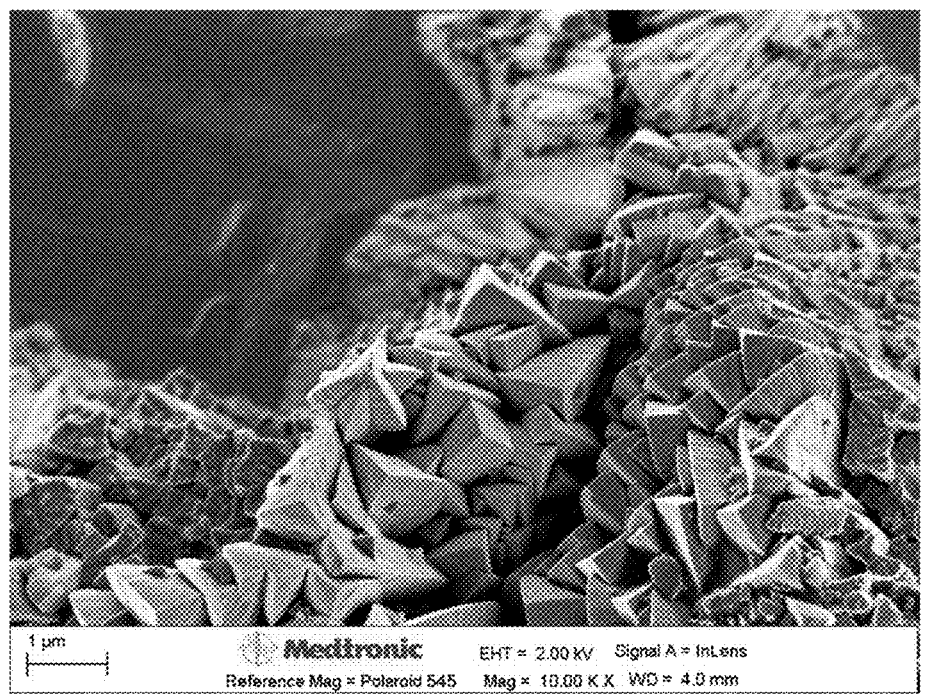
Figure 13D:
Figure 13E:
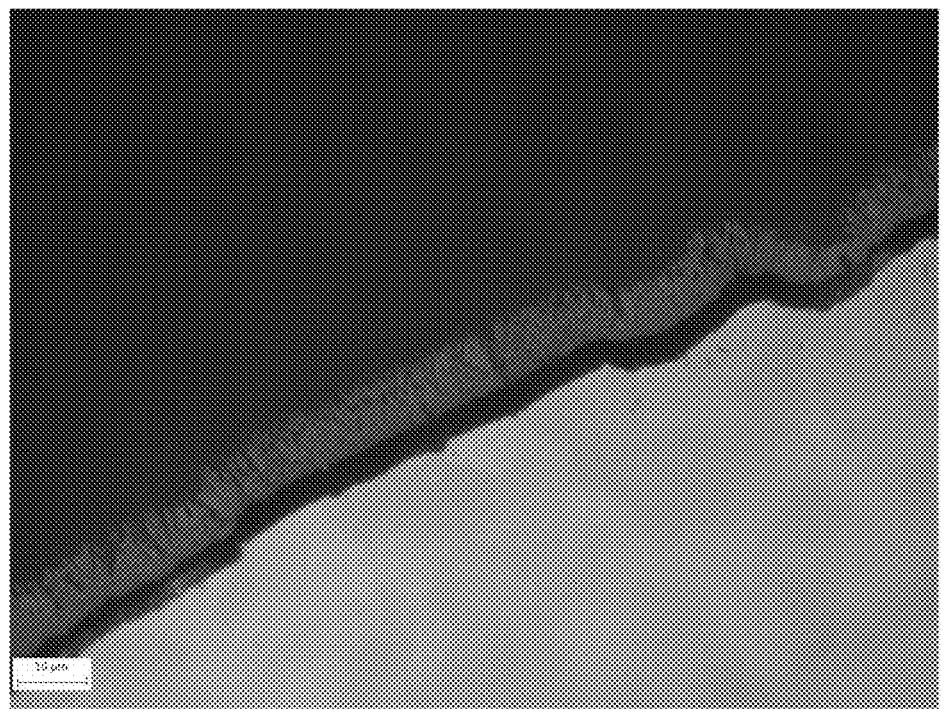
Figure 14A:
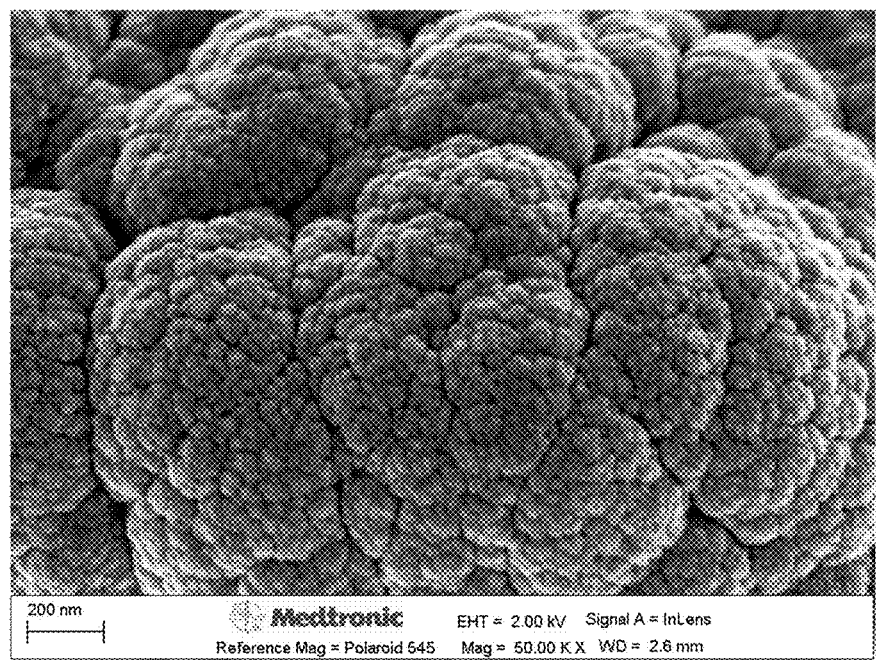
Figure 14B:
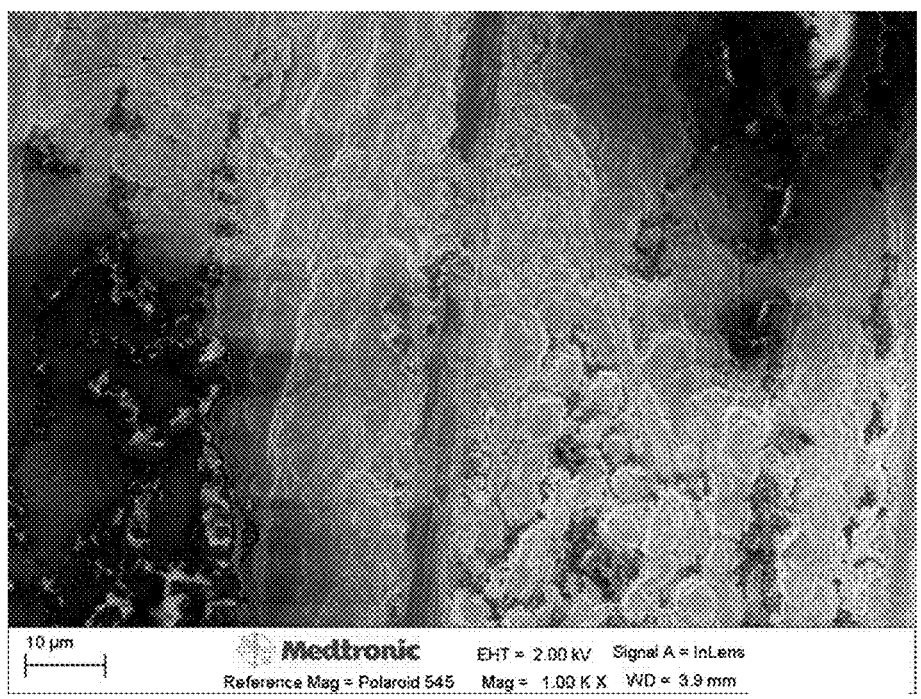
Figure 14C:
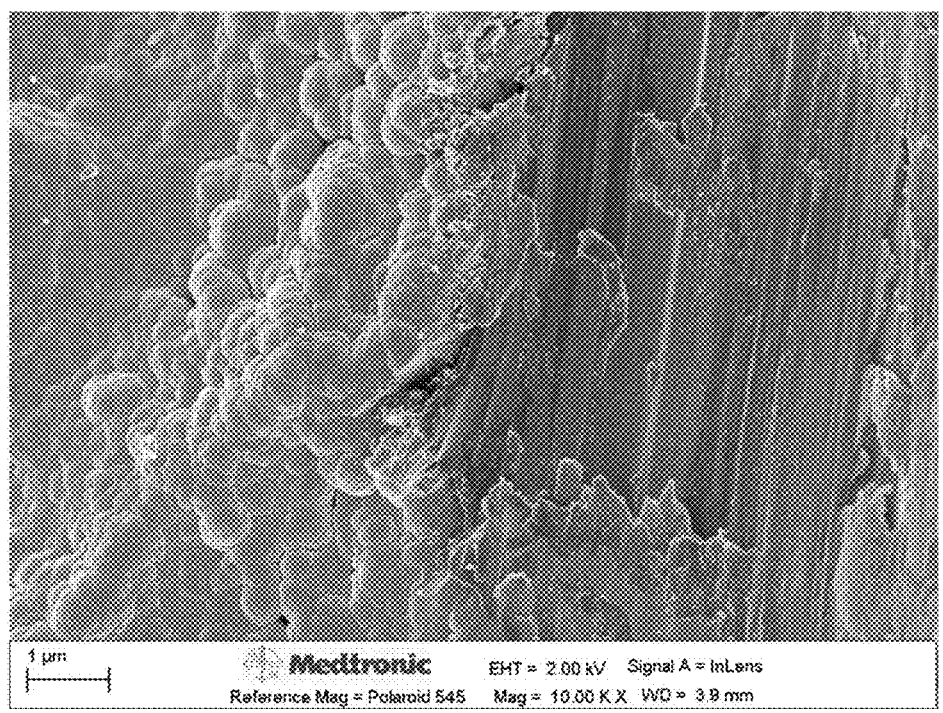
Figure 14D:
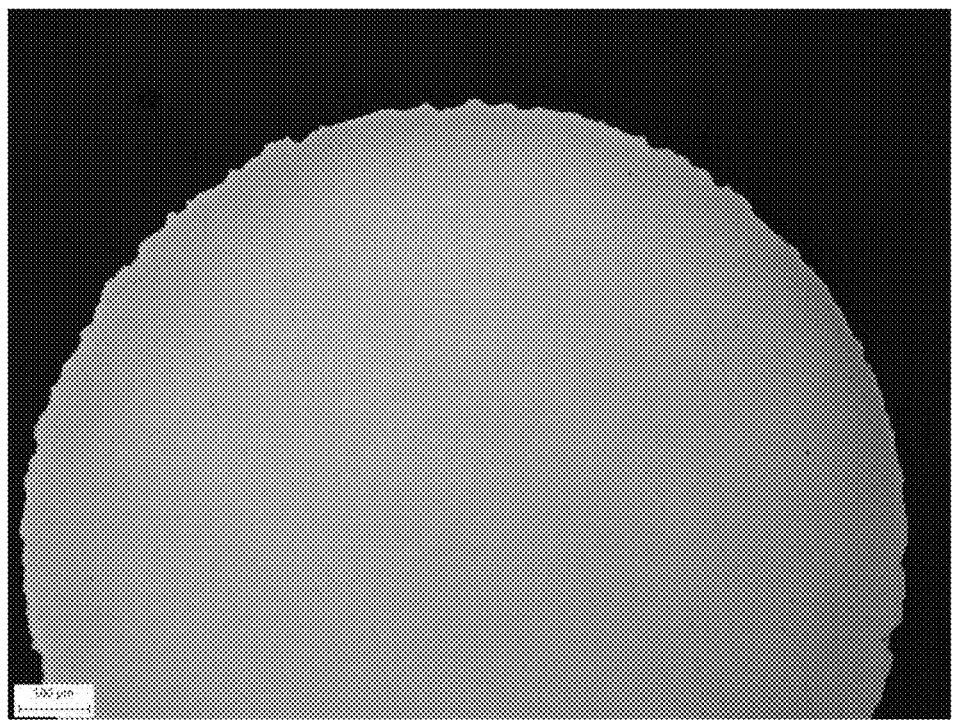
Figure 14E:
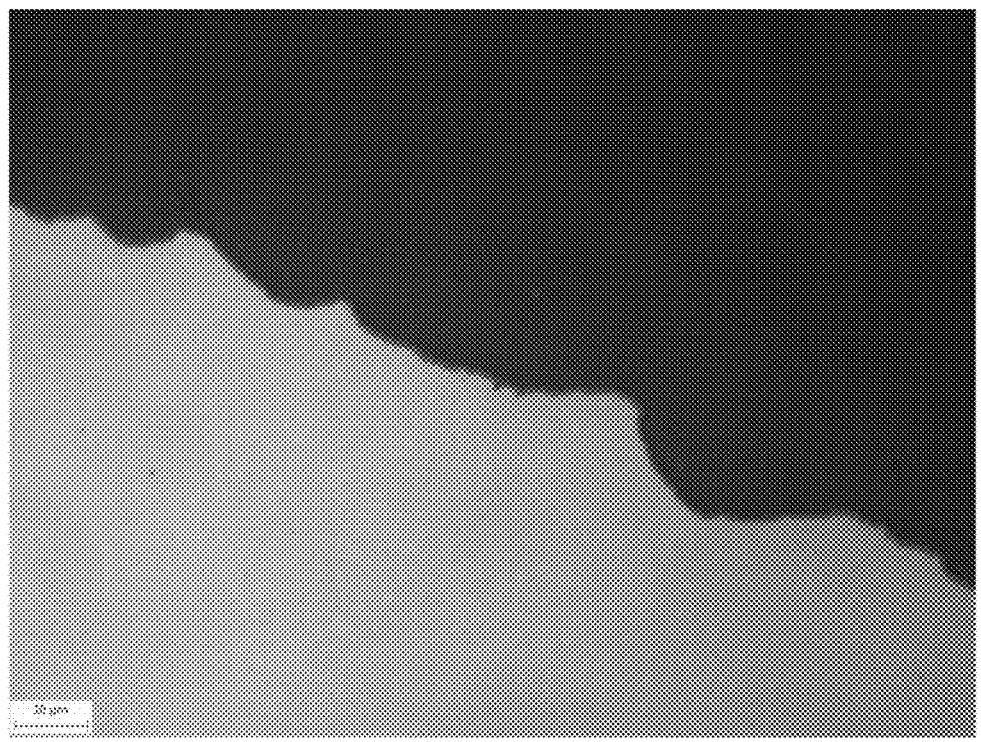
Figure 15A:
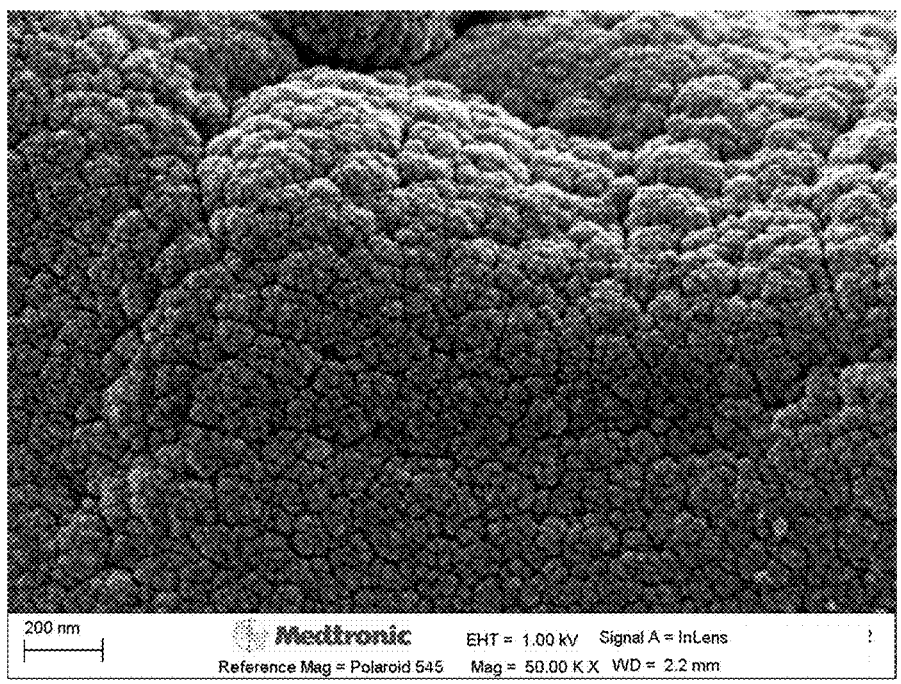
Figure 15B:
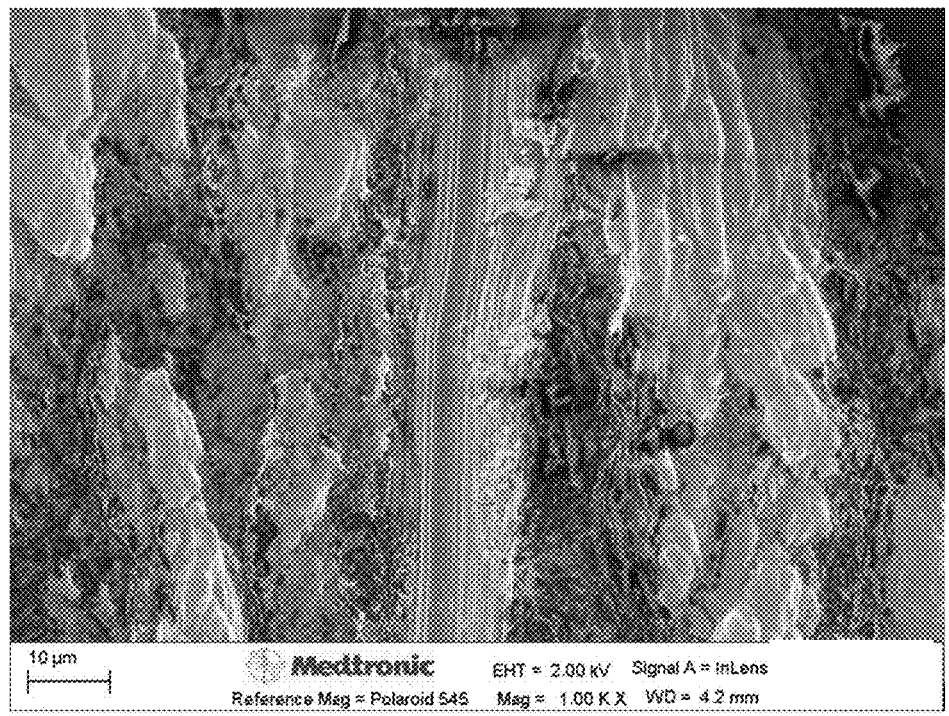
Figure 15C:
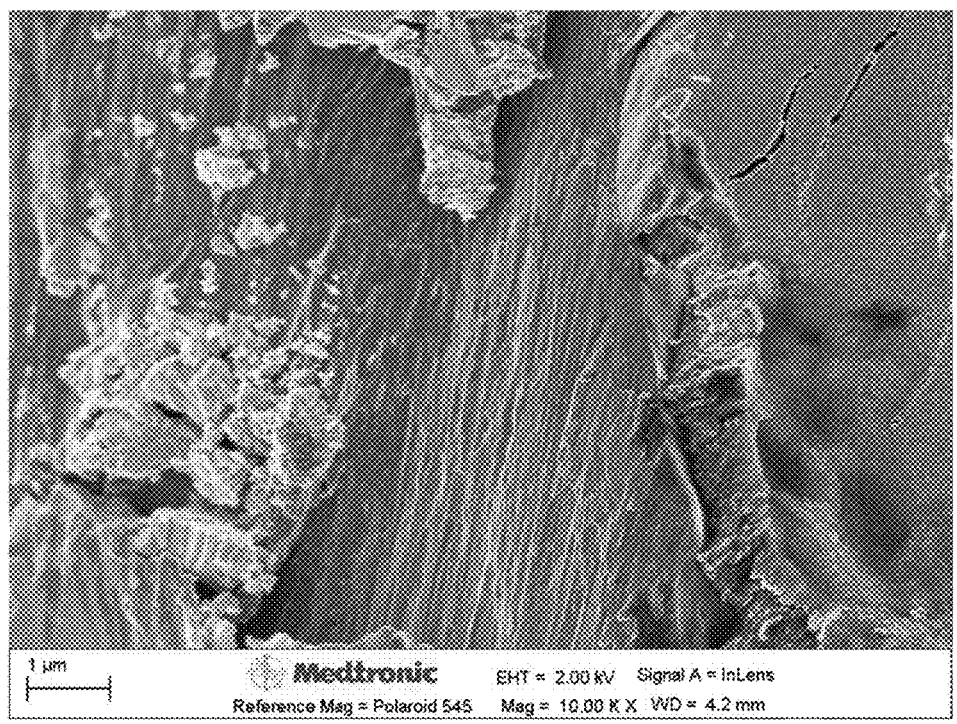
Figure 15D:
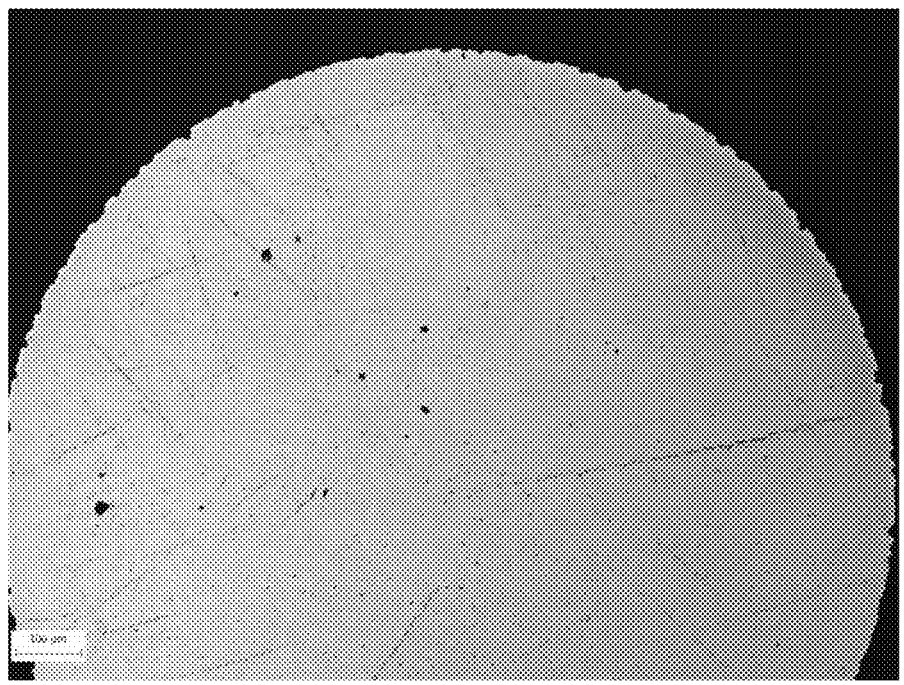
Figure 15E:
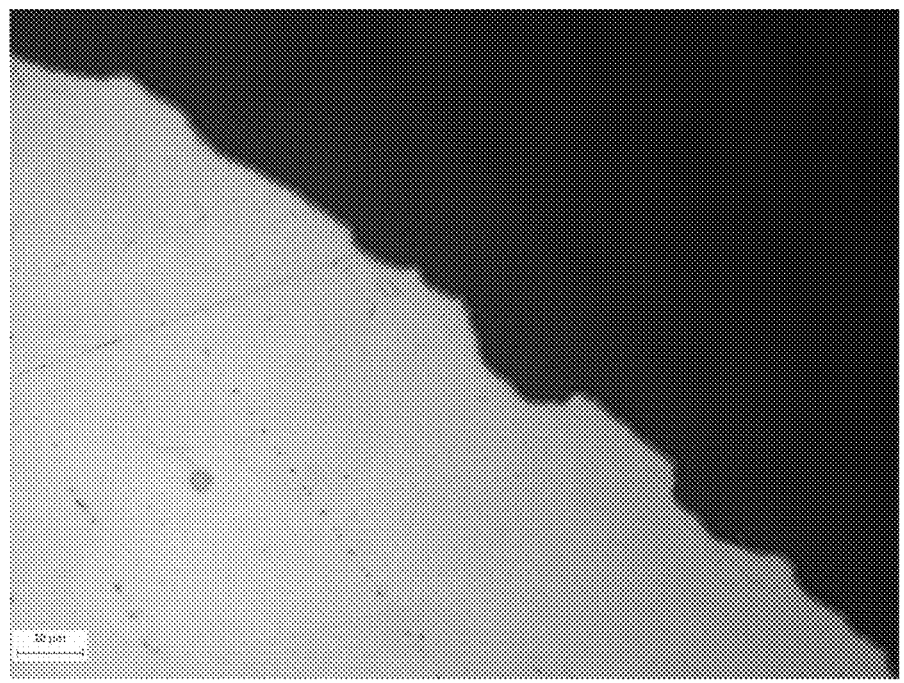

For each sample, high magnification scanning electron microscopy (SEM) images were taken of the surface of the coating. These images are shown in the first or "A" figures for the set of five figures corresponding to a sample, as indicated in the above table. For example, FIG. 6A is a SEM image of the surface of the approximately 2 μm Pt coating applied to the surface of the approximately 0.05 inch Ti-15Mo rod. As indicated by the SEM images, each sample including Pt or TiN coatings exhibited highly textured fractal morphology, vastly increasing effective surface area over a bare Pt electrode. The sputtered deposited IrOx coating had rough surface morphology.

The surface of the coated sample then underwent a ramping load microscratch test with a diamond tip, after which two SEM images were taking of the surface of the coating to evaluate the results of the test. These images are shown in the second and third images or "B" and "C" images for the set of five figures corresponding to a sample. As indicated by the SEM images, for each of the samples including a Pt or TiN coating, the coating was ductile and deformable. The microscratch tests showed that both Pt coating and TiN coating have very good adhesion to the substrate rods. Such results indicate that the risk of coating delamination/chipping-off is very low.

Finally, two cross-sectional optical images of each sample where taken. These images are shown in the fourth and fifth images or "D" and "E" images for the set of five figures corresponding to a sample. As indicated by the cross-sectional images, the coating for each sample exhibited a substantially uniform thickness and there was substantially consistent coverage throughout.

Figure 16:
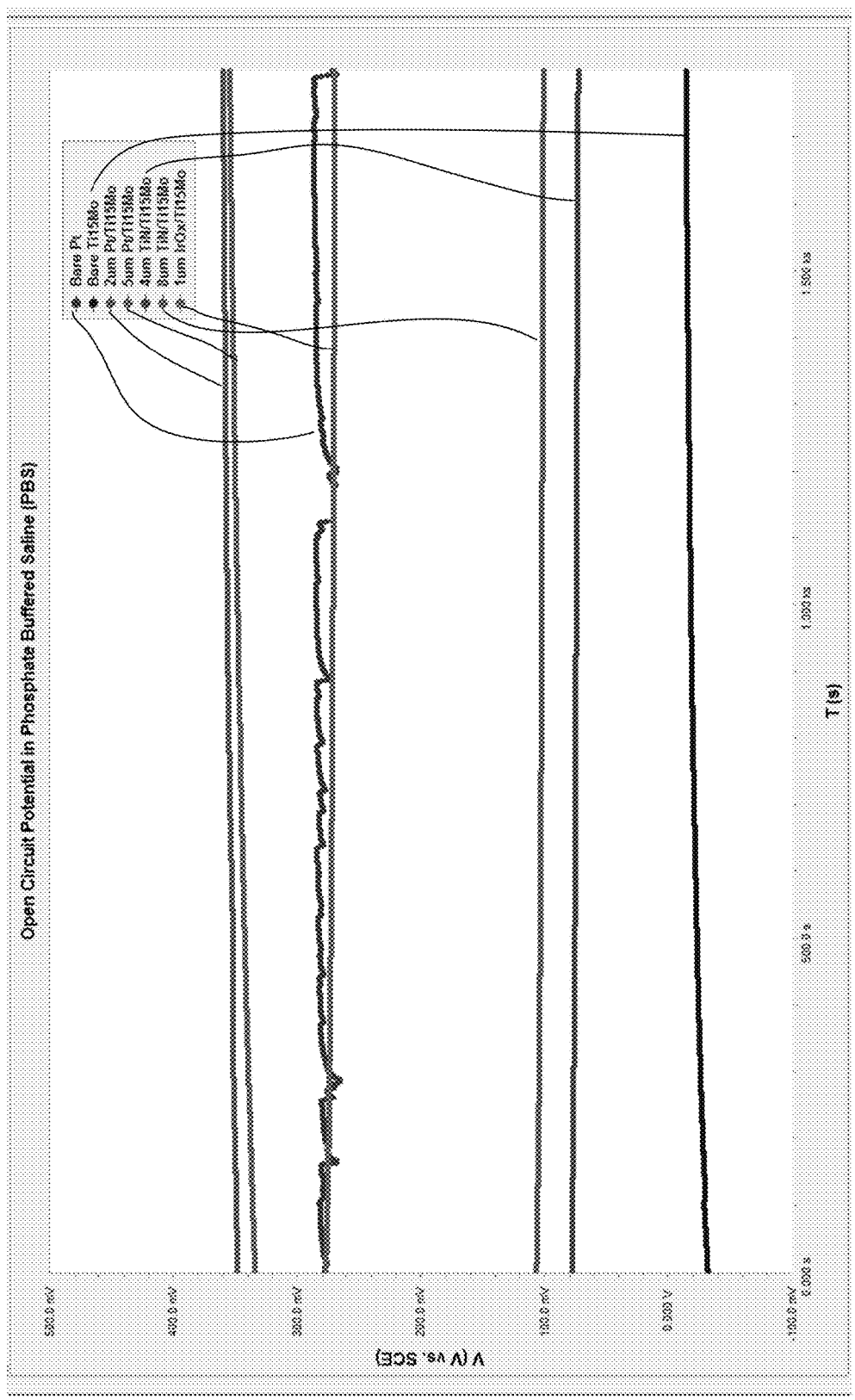
Figure 17:
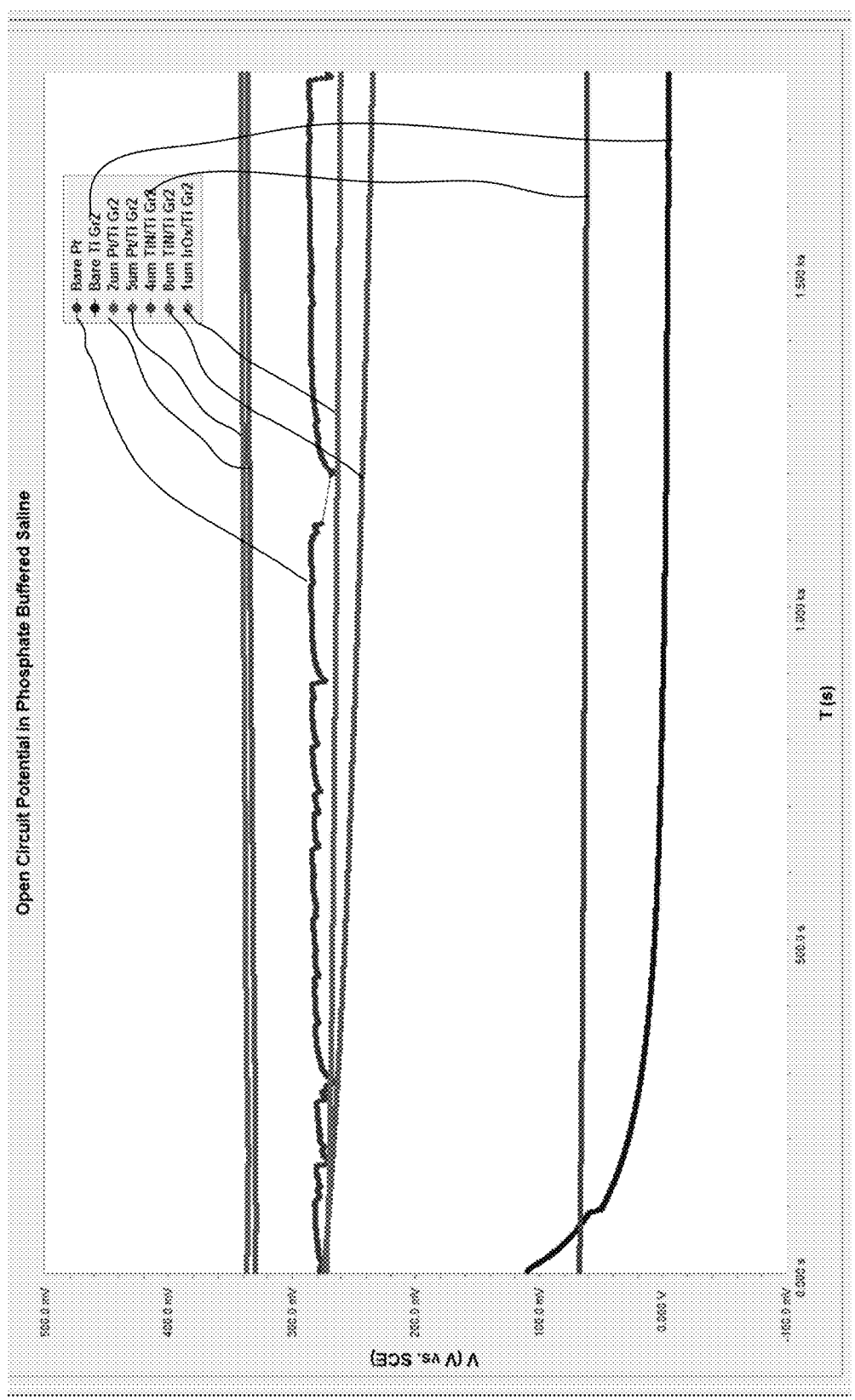

Various electrochemical tests were performed to evaluate each sample. FIG. 16 is a plot illustrating the open circuit potential of a bare Pt rod and bare Ti-15Mo rod versus the sample coated Ti-15Mo rods in the above table. FIG. 17 is a plot illustrating the open circuit potential of a bare Pt rod and bare Ti-Grade 2 rod versus the sample coated Ti-Grade 2 rods in the above table. As shown in FIGS. 16 and 17, both the Ti-15Mo and Ti Grade 2 rods displayed stable open circuit potentials and likely would not undergo active dissolution if substrate is exposed due to mechanical damage or defects (e.g. pinhole) in coating.

Figure 18:
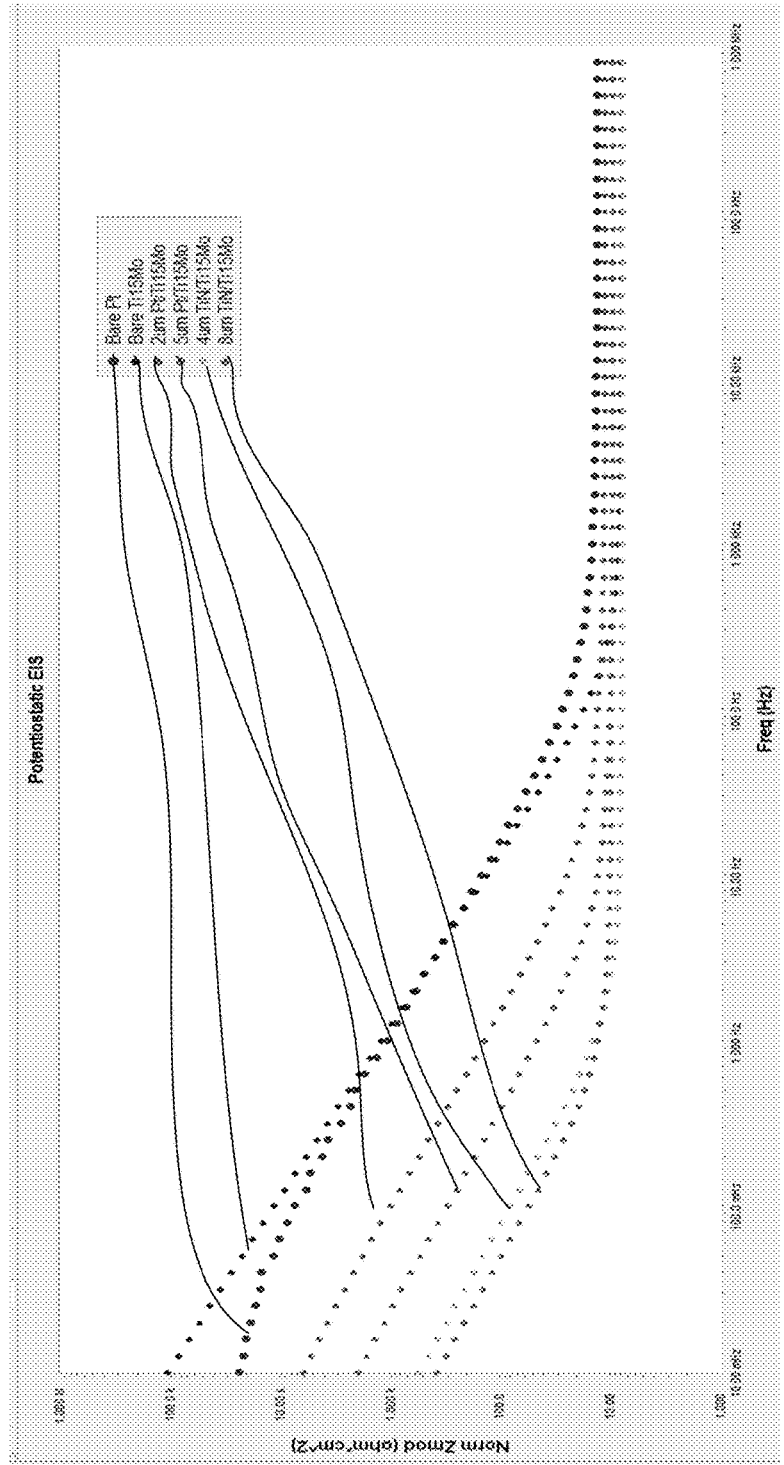

FIG. 18 is a bode plot generated using electrochemistry impedance spectroscopy (EIS) for a bare Pt rod and bare Ti-15Mo rod versus the sample Pt and TiN coated Ti-1.5Mo rods in the above table. As shown, the application of the Pt and TiN coatings reduced electrode impedance by about one-half order to about two orders of magnitude in the low frequency range.

Figure 19:
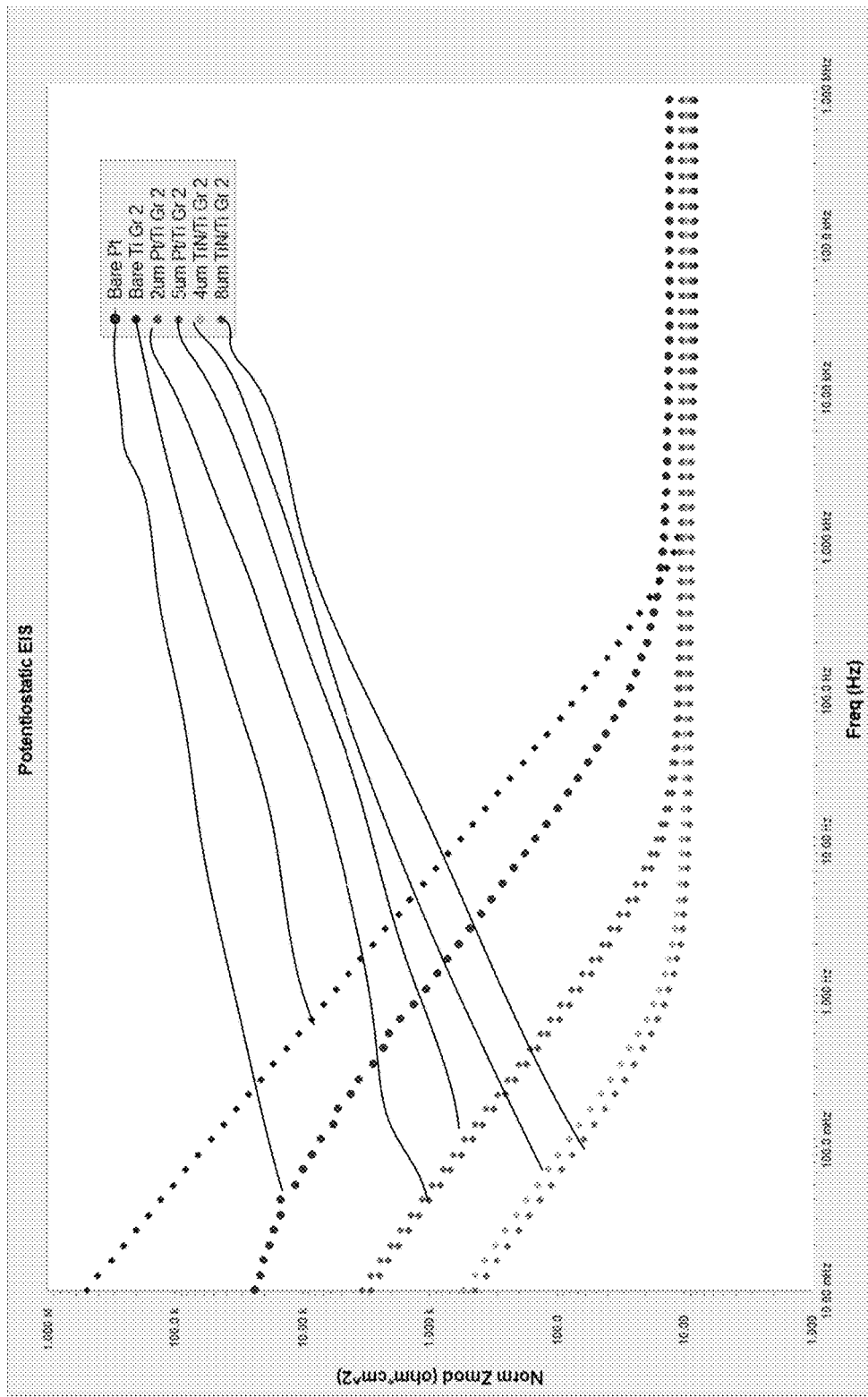

FIG. 19 is a bode plot generated using electrochemistry impedance spectroscopy (EIS) for a bare Pt rod and bare Ti-Grade 2 rod versus the sample Pt and TIN coated Ti-Grade rods in the above table. Again, as shown, the application of the Pt and TiN coatings reduced electrode impedance by about one-half order to about two orders of magnitude in the low frequency range.

Figure 20:
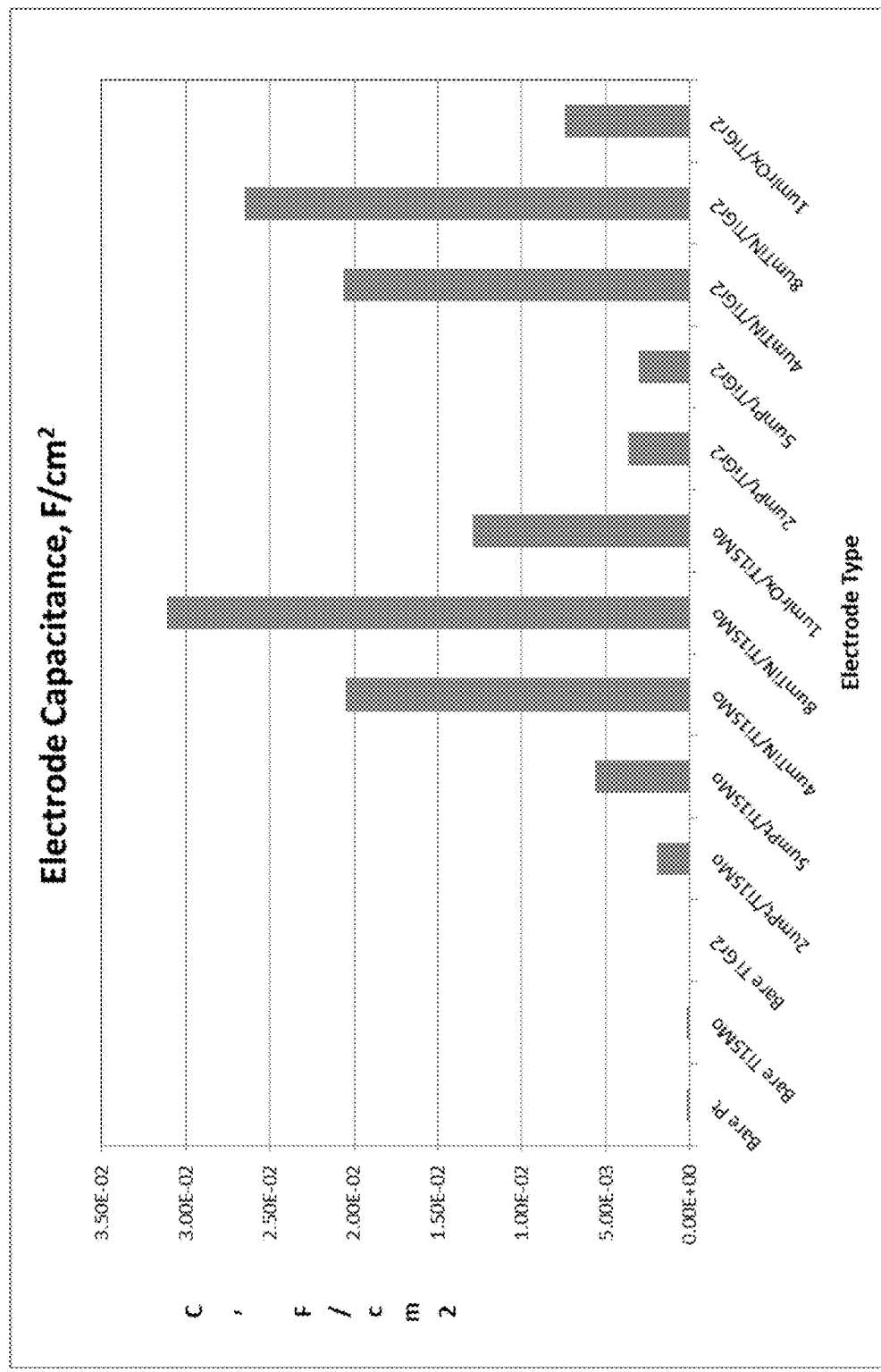

FIG. 20 is a bar chart illustrating the electrode capacitance determined for each sample as well as bare Pt, bare Ti-15Mo, and bare Ti-Grade 2 rods. As shown, the application of the coating to the sample rods improved electrode capacitance by a minimum of one order of magnitude.

Figure 21:
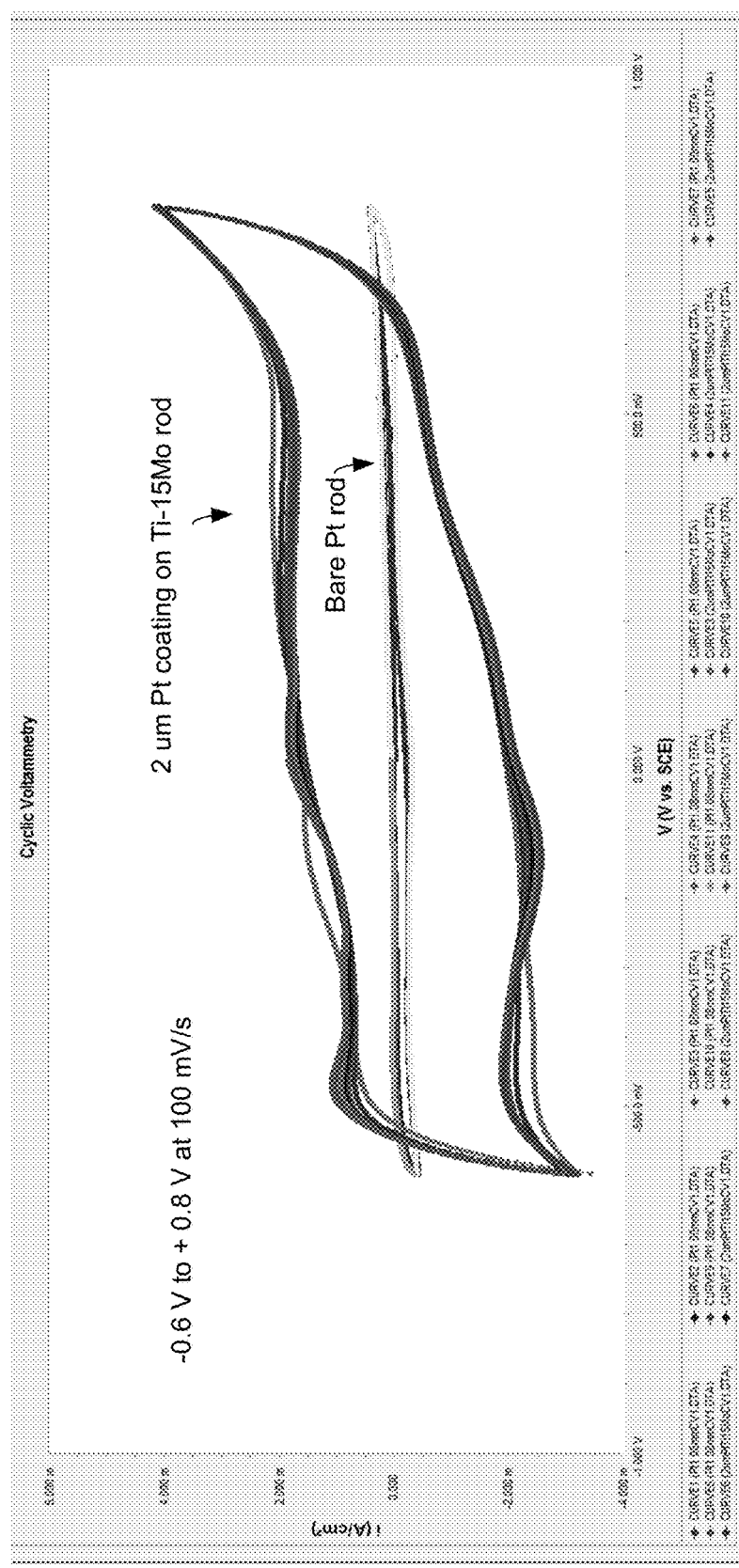
Figure 22:
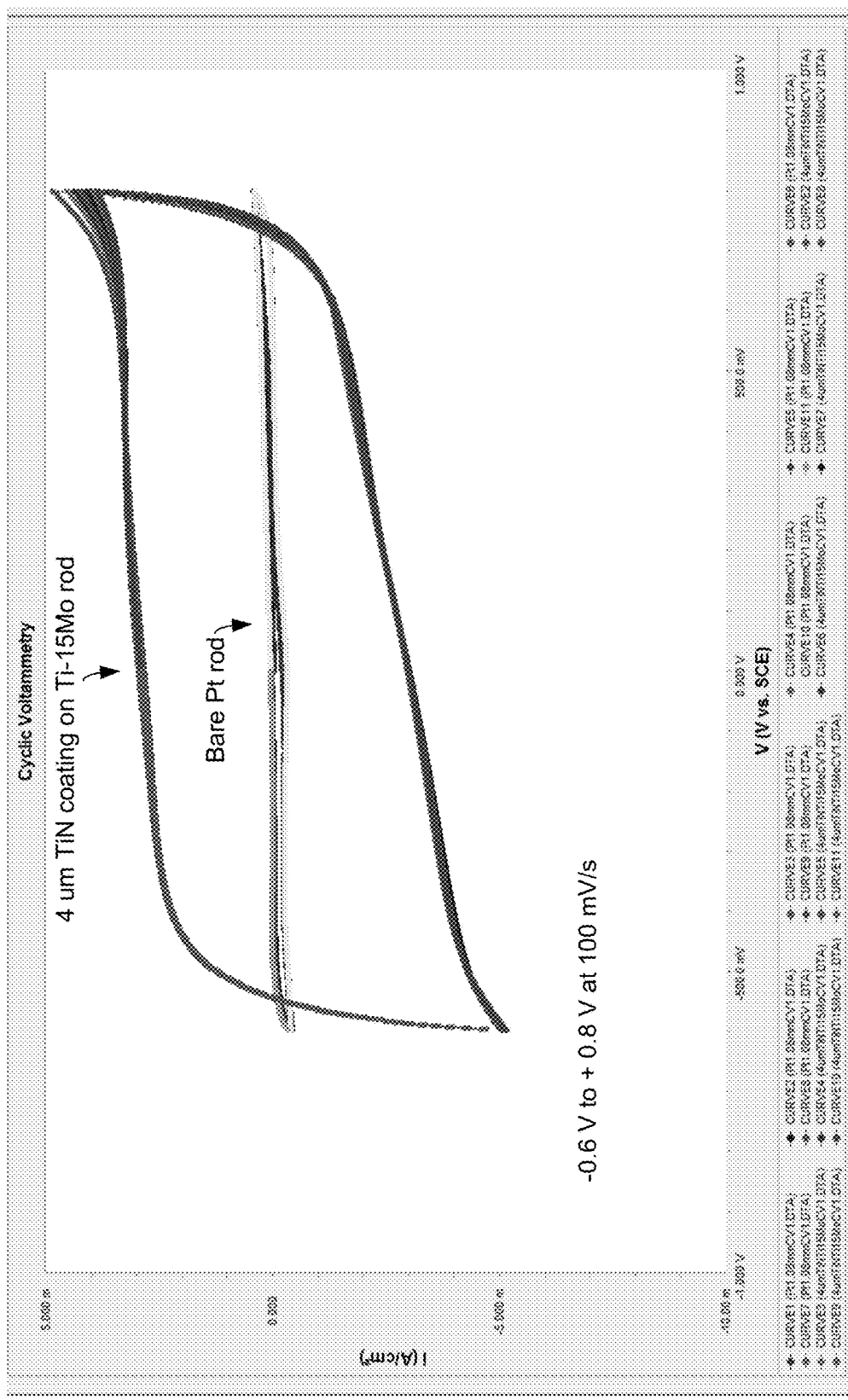

FIG. 21 is a plot comparing the cyclic voltammogram for the sample Ti-15Mo rod with a 2 μm Pt coating versus bare Pt rod. FIG. 22 is a plot comparing the cyclic voltammogram for the sample Ti-15Mo rod with a 4 μm TiN coating. As shown in FIGS. 21 and 22, there was a significant increase in charge storage capacity when the substrates were coated, which is desirable.

Figure 23:
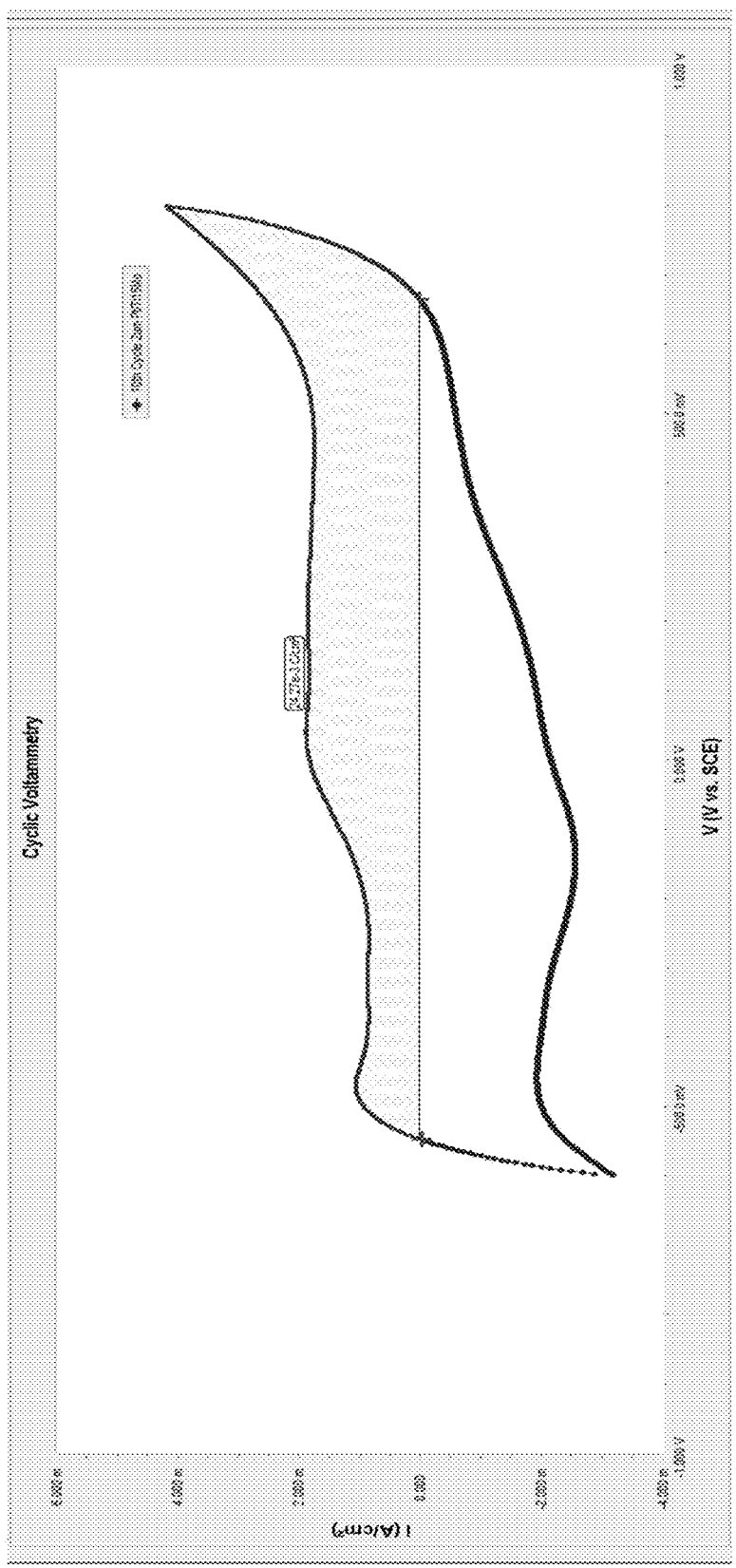

FIG. 23 is a plot of charge storage capacity for the Ti15Mo rod with a 2 μm Pt coating determined based on the voltammogram of FIG. 21. The anodic charge storage capacity was determined to be approximately 24.27 mC/cm$^2$. The cathodic charge storage capacity was determined to be approximately −22.76 mC/cm$^2$ for a total charge storage capacity of approximately 47.03 mC/cm$^2$ determined for the sample.

Figure 24:
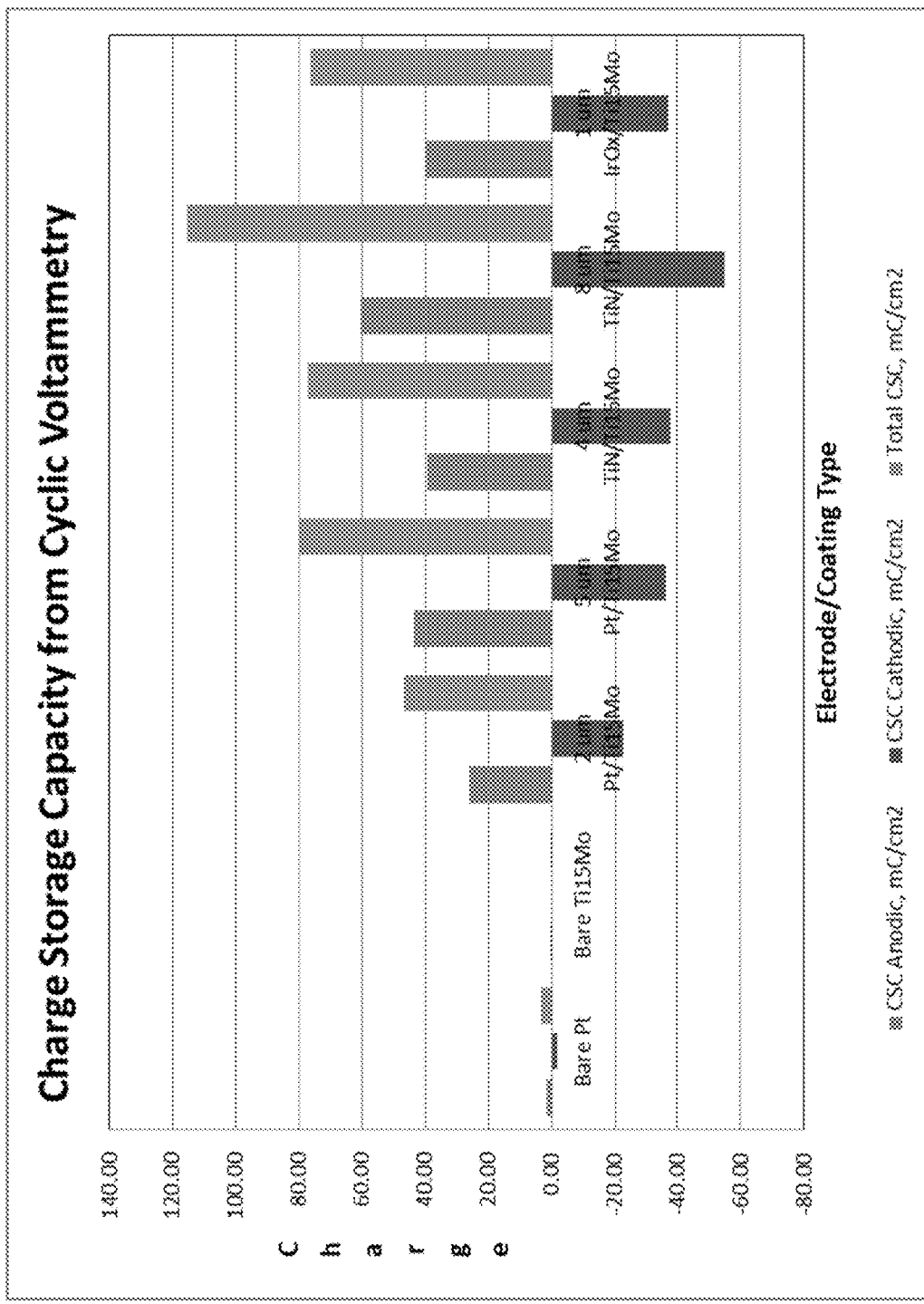

FIG. 24 is a bar chart summarizing the charge storage capacity determined for each sample coated Ti-15Mo rod along with a bare Pt and bare Ti-15Mo rod. For each sample on the bar chart, the first bar, moving left to right, corresponds to the anodic charge storage capacity, the second bar corresponds to the cathodic charge storage capacity, and the third bar corresponds to the total charge storage capacity. As indicated by the results, the application of the example coatings on the Ti-15Mo rods increased the charge storage capacity for all sample by a minimum of one order of magnitude compared to the bare rods.

Figure 25:
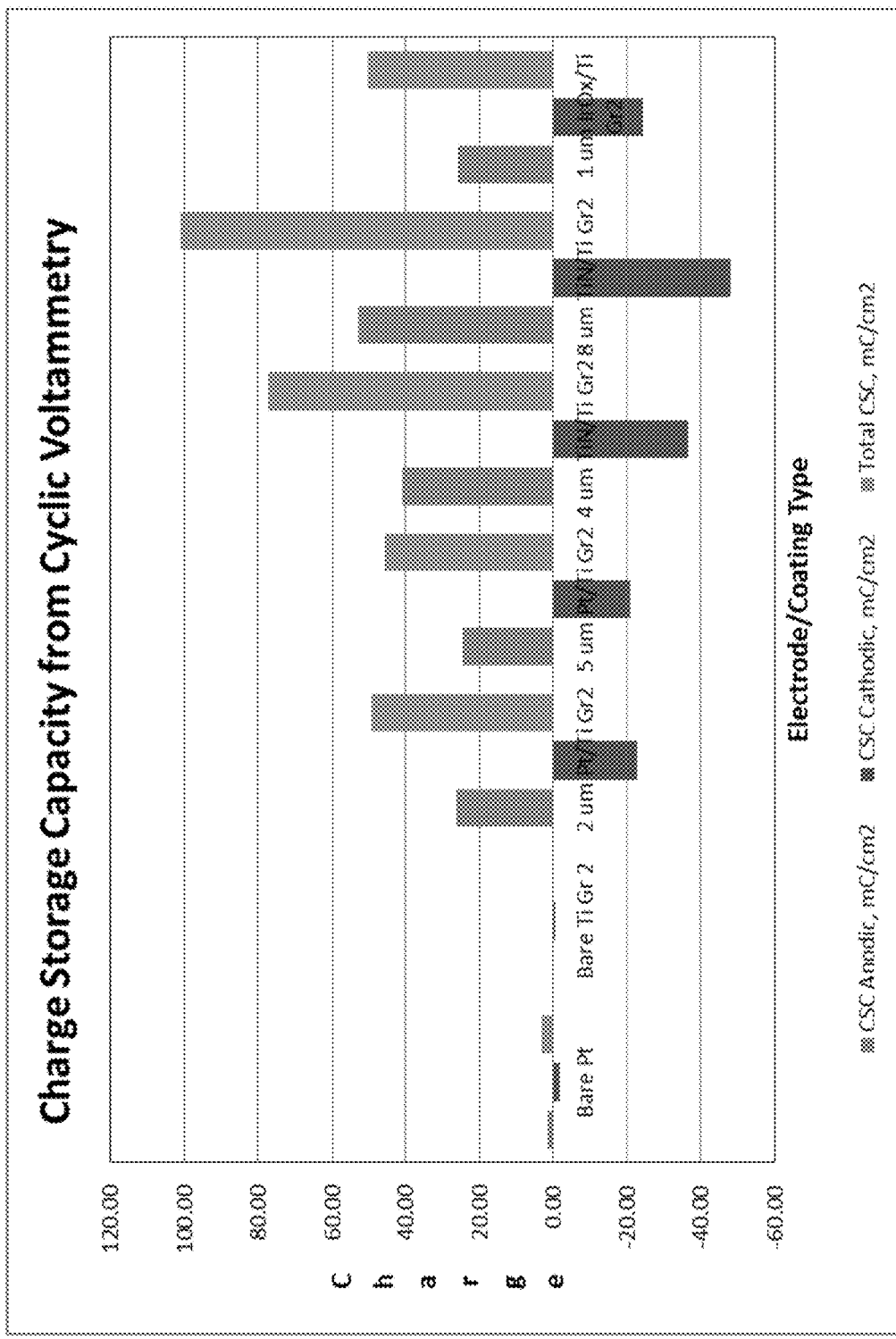

FIG. 25 is a bar chart summarizing the charge storage capacity determined for each sample coated Ti-Grade 2 rod along with a bare Pt and bare Ti-Grade 2 rod. For each sample on the bar chart, the first bar, moving left to right, corresponds to the anodic charge storage capacity, the second bar corresponds to the cathodic charge storage capacity, and the third bar corresponds to the total charge storage capacity. As indicated by the results, the application of the example coatings on the Ti-Grade 2 rods increased the charge storage capacity for all sample by a minimum of one order of magnitude compared to the bare rods.

Various examples of the disclosure have been described. These and other examples are within the scope of the following claims.

The invention claimed is:
1. A medical device comprising:
   a lead including an electrically conductive lead wire; and an electrode electrically coupled to the lead wire, the electrode including a substrate and a coating on an outer surface of the substrate, wherein the lead wire is formed of a composition comprising titanium or titanium alloy, wherein the substrate is formed of a composition comprising one or more of titanium, tantalum, niobium, or an alloy thereof, wherein the coating comprises at least one of Pt, TiN, IrOx, or poly(dioctyl-bithiophene) (PDOT).

2. The medical device of claim 1, wherein the lead wire and substrate are formed of different compositions.

3. The medical device of claim 1, wherein the coating defines a thickness of between approximately 0.5 micrometers and approximately 15 micrometers.

4. The medical device of claim 1, wherein the composition of the lead wire comprises the titanium alloy, wherein the titanium alloy includes titanium and molybdenum.

5. The medical device of claim 1, wherein the coating is deposited on the outer surface of the substrate via sputter depositing to increase the effective surface area of the outer surface of the substrate.

6. The medical device of claim 1, wherein the electrode is one of a ring electrode or segmented electrode.

7. The medical device of claim 1, wherein the electrode exhibits a charge storage capacity of greater than approximately 50 $mC/cm^2$.

8. The medical device of claim 1, wherein the lead wire and substrate are formed of substantially a same composition.

9. The medical device of claim 1, wherein the lead wire and the substrate are coupled to each other via a laser weld or resistance weld.

10. The medical device of claim 1, further comprising a medical device including an electrical stimulation generator, wherein the lead wire is configured to be electrically coupled to the stimulation generator such that electrical stimulation signals may be transmitted from the electrical stimulation generator through the coating on the substrate via the lead wire.

11. A method for forming a medical device lead, the method comprising:
electrically coupling a lead including an electrically conductive lead wire to an electrode, the electrode comprising a substrate having an outer surface; and
depositing a coating on the outer surface of the substrate, wherein the lead wire is formed of a composition comprising titanium or titanium alloy, wherein the substrate is formed of a composition comprising one or more of titanium, tantalum, niobium, or an alloy thereof, wherein the coating comprises at least one of Pt, TiN, IrOx, or poly(dioctyl-bithiophene) (PDOT).

12. The method of claim 11, wherein the lead wire and substrate are formed of different compositions.

13. The method of claim 11, wherein the coating defines a thickness of between approximately 0.5 micrometers and approximately 15 micrometers.

14. The method of claim 11, wherein the composition of the lead wire comprises the titanium alloy, wherein the titanium alloy comprises titanium and molybdenum.

15. The method of claim 11, wherein the coating is deposited on the outer surface of the substrate via sputter depositing to increase the effective surface area of the outer surface of the substrate.

16. The method of claim 11, wherein the electrode is one of a ring electrode or segmented electrode.

17. The method of claim 11, wherein the electrode exhibits a charge storage capacity of greater than approximately 50 $mC/cm^2$.

18. The method of claim 11, wherein the lead wire and substrate are formed of substantially a same composition.

19. The method of claim 11, wherein the lead wire and the substrate are coupled to each other via a laser weld or a resistance weld.

20. The method of claim 11, further comprising a medical device including an electrical stimulation generator, wherein the lead wire is configured to be electrically coupled to the stimulation generator such that electrical stimulation signals may be transmitted from the electrical stimulation generator through the coating on the substrate via the lead wire.

21. The medical device of claim 1, wherein the coating comprises at least one of TiN, IrOx, or PDOT.

22. The medical device of claim 1, wherein the lead wire extends distally within the lead from a proximal end of the lead to the electrode, and wherein the lead wire is configured to electrically couple the electrode to an electrical stimulation generator such that electrical stimulation signals may be transmitted from the electrical stimulation generator through the coating on the substrate via the lead wire.

23. The medical device of claim 1, wherein the electrode comprises a first electrode, the substrate comprises a first substrate, and the coating comprises a first coating, wherein the lead further includes a second electrically conductive lead wire electrically isolated from the first electrically conductive lead wire, the medical device further comprising a second electrode electrically coupled to the second electrically conductive lead wire, wherein the second electrode comprises a second substrate and a second coating on an outer surface of the second substrate, wherein the second electrically conductive lead wire is formed of a second composition comprising titanium or titanium alloy, wherein the second substrate is formed of a second composition comprising one or more of titanium, tantalum, niobium, or an alloy thereof, and wherein the second coating comprises at least one of Pt, TiN, IrOx, or poly(dioctyl-bithiophene) (PDOT).

24. The medical device of claim 23, wherein the first substrate is disposed at a location on the lead distal to a location of the second substrate.

25. The medical device of claim 23, wherein the first electrode and the second electrode each extend distally to substantially a same length from a proximal end of the lead.

26. The method of claim 11, wherein the coating comprises at least one of TiN, IrOx, or PDOT.

27. The method of claim 11, wherein the lead wire extends distally within the lead from a proximal end of the lead to the electrode, and wherein the lead wire is configured to electrically couple the electrode to an electrical stimulation generator such that electrical stimulation signals may be transmitted from the electrical stimulation generator through the coating on the substrate via the lead wire.

28. The method of claim 11, wherein the electrode comprises a first electrode, the substrate comprises a first substrate, and the coating comprises a first coating, and wherein the second electrically conductive lead wire is electrically isolated from the first electrically conductive lead wire, the method further comprising:
electrically coupling the lead to a second electrode by coupling a second electrically conductive lead wire to the second electrode, the second electrode comprising a second substrate having an outer surface; and
depositing a second coating on the outer surface of the second substrate, wherein the second electrically conductive lead wire is formed of a composition comprising titanium or titanium alloy, wherein the second substrate is formed of a composition comprising one or more of titanium, tantalum, niobium, or an alloy thereof, and wherein the second coating comprises at least one of Pt, TiN, IrOx, or poly(dioctyl-bithiophene) (PDOT).

29. The method of claim 28, wherein the first substrate is disposed at a location on the lead distal to a location of the second substrate.

30. The method of claim 28, wherein the first electrode and the second electrode each extend distally to substantially a same length from a proximal end of the lead.

* * * * *